US009102654B2

(12) United States Patent
Yang et al.

(10) Patent No.: US 9,102,654 B2
(45) Date of Patent: Aug. 11, 2015

(54) PROCESSES FOR THE PREPARATION OF PESTICIDAL COMPOUNDS

(71) Applicant: Dow AgroSciences LLC, Indianapolis, IN (US)

(72) Inventors: Qiang Yang, Zionsville, IN (US); Beth Lorsbach, Indianapolis, IN (US); Gary Roth, Midland, MI (US); Noormohamed M. Niyaz, Indianapolis, IN (US); Jeffrey Nissen, Indianapolis, IN (US); Ronald Ross, Jr., Zionsville, IN (US); Gregory T. Whiteker, Carmel, IN (US); Carl DeAmicis, Indianapolis, IN (US); Kaitlyn Gray, Freeland, MI (US); Yu Zhang, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/517,587

(22) Filed: Oct. 17, 2014

(65) Prior Publication Data

US 2015/0112077 A1    Apr. 23, 2015

Related U.S. Application Data

(60) Provisional application No. 62/042,559, filed on Aug. 27, 2014, provisional application No. 62/001,928, filed on May 22, 2014, provisional application No. 61/892,132, filed on Oct. 17, 2013.

(51) Int. Cl.
*C07D 401/04* (2006.01)
*C07D 213/77* (2006.01)
*A01N 43/56* (2006.01)

(52) U.S. Cl.
CPC .............. *C07D 401/04* (2013.01); *A01N 43/56* (2013.01); *C07D 213/77* (2013.01)

(58) Field of Classification Search
CPC ..................................................... C07D 401/04
USPC ...................................................... 546/275.4
See application file for complete search history.

(56) References Cited

U.S. PATENT DOCUMENTS

| 4,080,457 | A | 3/1978 | Harrison et al. |
|---|---|---|---|
| 4,260,765 | A | 4/1981 | Harrison et al. |
| 4,536,506 | A | 8/1985 | Marcoux et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony et al. |
| 5,869,681 | A | 2/1999 | Muller et al. |
| 6,218,418 | B1 | 4/2001 | Pevarello et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 7,192,906 | B2 | 3/2007 | Hirohara et al. |
| 7,196,104 | B2 | 3/2007 | Askew, Jr. et al. |
| 7,319,108 | B2 | 1/2008 | Schwink et al. |
| 7,774,978 | B2 | 8/2010 | Ding et al. |
| 7,803,832 | B2 | 9/2010 | Critcher et al. |
| 7,910,606 | B2 | 3/2011 | Nazare et al. |
| 7,923,573 | B2 | 4/2011 | Tamaki et al. |
| 8,163,756 | B2 | 4/2012 | Flynn et al. |
| 8,222,280 | B2 | 7/2012 | Liu et al. |
| 8,901,153 | B2 | 12/2014 | Buysse et al. |
| 2002/0013326 | A1 | 1/2002 | Tiebes et al. |
| 2003/0153464 | A1 | 8/2003 | Nakamura et al. |
| 2003/0213405 | A1 | 11/2003 | Harada et al. |
| 2004/0082629 | A1 | 4/2004 | Iwataki et al. |
| 2005/0038059 | A1 | 2/2005 | Mueller et al. |
| 2005/0176710 | A1 | 8/2005 | Schwink et al. |
| 2006/0160857 | A1 | 7/2006 | Buettelmann et al. |
| 2006/0160875 | A1 | 7/2006 | Gaines et al. |
| 2007/0167426 | A1 | 7/2007 | Siddiqui et al. |
| 2008/0004301 | A1 | 1/2008 | Tamaki et al. |
| 2008/0027046 | A1 | 1/2008 | Annan et al. |
| 2009/0069288 | A1 | 3/2009 | Breinlinger et al. |
| 2009/0137524 | A1 | 5/2009 | Billen et al. |
| 2009/0325956 | A1 | 12/2009 | Taniguchi et al. |
| 2010/0130474 | A1 | 5/2010 | Bothmann et al. |
| 2010/0204164 | A1 | 8/2010 | Crouse et al. |
| 2010/0292253 | A1 | 11/2010 | Trullinger et al. |
| 2010/0305200 | A1 | 12/2010 | Velicelebi et al. |
| 2011/0021771 | A1 | 1/2011 | Mallais et al. |

(Continued)

FOREIGN PATENT DOCUMENTS

| EP | 0097323 | A2 | 1/1984 |
|---|---|---|---|
| EP | 0205024 | A2 | 12/1986 |
| EP | 0248315 | A2 | 12/1987 |
| EP | 0425948 | A2 | 5/1991 |
| EP | 1273582 | A1 | 1/2003 |
| EP | 1321463 | A1 | 6/2003 |
| EP | 1329160 | A2 | 7/2003 |
| JP | 1987-153273 | A | 7/1987 |
| JP | 1988-174905 | A | 7/1988 |
| JP | 1989-226815 | A | 9/1989 |
| JP | 2003-212864 | A | 7/2003 |
| JP | 2004-051628 | A | 2/2004 |
| JP | 2004-292703 | A | 10/2004 |
| JP | 2012-188418 | A | 10/2012 |
| JP | 2013-075871 | A | 4/2013 |
| JP | 2013-082699 | A | 5/2013 |
| JP | 2013-082704 | A | 5/2013 |
| JP | 2013-107867 | A | 6/2013 |
| JP | 2013-129651 | A | 7/2013 |

(Continued)

OTHER PUBLICATIONS

International Preliminary Report on Patentability for PCT/US2011/058578 mailed Dec. 21, 2012.

(Continued)

*Primary Examiner* — Patricia L Morris
(74) *Attorney, Agent, or Firm* — Carl D. Corvin; Barnes & Thornburg LLP

(57) ABSTRACT

The present application provides processes for making pesticidal compounds and compounds useful both as pesticides and in the making of pesticidal compounds.

7 Claims, No Drawings

(56) References Cited

U.S. PATENT DOCUMENTS

| | | |
|---|---|---|
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fu Lein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0220453 A1 | 8/2012 | Lowe et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |

FOREIGN PATENT DOCUMENTS

| | | |
|---|---|---|
| JP | 2013-129653 A | 7/2013 |
| WO | WO 94/13644 A1 | 6/1994 |
| WO | WO 97/36897 A1 | 10/1997 |
| WO | WO 98/49166 A1 | 11/1998 |
| WO | WO 00/35919 A2 | 6/2000 |
| WO | WO 01/34127 A1 | 5/2001 |
| WO | WO 01/90078 A1 | 11/2001 |
| WO | WO 02/083111 A2 | 10/2002 |
| WO | WO 03/008405 A1 | 1/2003 |
| WO | WO 03/072102 A1 | 9/2003 |
| WO | WO 2004/041813 A1 | 5/2004 |
| WO | WO 2005/070925 A1 | 8/2005 |
| WO | WO 2005/074875 A2 | 8/2005 |
| WO | WO 2006/023462 A1 | 3/2006 |
| WO | WO 2006/033005 A2 | 3/2006 |
| WO | WO 2006/046593 A1 | 5/2006 |
| WO | WO 2006/103045 A1 | 10/2006 |
| WO | WO 2007/005838 A2 | 1/2007 |
| WO | WO 2007/087427 A2 | 8/2007 |
| WO | WO 2007/098826 A2 | 9/2007 |
| WO | WO 2008/005457 A2 | 1/2008 |
| WO | WO 2008/079277 A1 | 7/2008 |
| WO | WO 2008/090382 A1 | 7/2008 |
| WO | WO 2009/149858 A1 | 12/2009 |
| WO | WO 2010/006713 A2 | 1/2010 |
| WO | WO 2010/009290 A1 | 1/2010 |
| WO | WO 2010/012442 A2 | 2/2010 |
| WO | WO 2010/033360 A1 | 3/2010 |
| WO | WO 2010/048207 A2 | 4/2010 |
| WO | WO 2010/060379 A1 | 6/2010 |
| WO | WO 2010/075376 A2 | 7/2010 |
| WO | WO 2010/129497 A1 | 11/2010 |
| WO | WO 2010/133336 A1 | 11/2010 |
| WO | WO 2010/146236 A1 | 12/2010 |
| WO | WO 2011/003065 A2 | 1/2011 |
| WO | WO 2011/043371 A1 | 4/2011 |
| WO | WO 2011/045224 A1 | 4/2011 |
| WO | WO 2011/045240 A1 | 4/2011 |
| WO | WO 2011/091153 A1 | 7/2011 |
| WO | WO 2011/101229 A1 | 8/2011 |
| WO | WO 2011/126903 A2 | 10/2011 |
| WO | WO 2011/128304 A1 | 10/2011 |
| WO | WO 2011/134964 A1 | 11/2011 |
| WO | WO 2011/138285 A1 | 11/2011 |
| WO | WO 2011/163518 A1 | 12/2011 |
| WO | WO 2012/000896 A2 | 1/2012 |
| WO | WO 2012/004217 A1 | 1/2012 |
| WO | WO 2012/007500 A2 | 1/2012 |
| WO | WO 2012/035011 A1 | 3/2012 |
| WO | WO 2012/052412 A1 | 4/2012 |
| WO | WO 2012/061290 A2 | 5/2012 |
| WO | WO 2012/070114 A1 | 5/2012 |
| WO | WO 2012/102387 A1 | 8/2012 |
| WO | WO 2012/108511 A1 | 8/2012 |
| WO | WO 2012/168361 A1 | 12/2012 |
| WO | WO 2013/000931 A1 | 1/2013 |
| WO | WO 2013/010946 A2 | 1/2013 |
| WO | WO 2013/010947 A2 | 1/2013 |
| WO | WO 2013/062980 A1 | 5/2013 |
| WO | WO 2013/156431 A1 | 10/2013 |
| WO | WO 2013/156433 A1 | 10/2013 |

OTHER PUBLICATIONS

International Search Report and Written Opinion for PCT/US2011/058578 mailed Apr. 5, 2012.

International Search Report and Written Opinion for PCT/US2013/029615 mailed May 8, 2013.

PROCESSES FOR THE PREPARATION OF PESTICIDAL COMPOUNDS

CROSS REFERENCE TO RELATED APPLICATIONS

This application claims the benefit of the following U.S. Provisional Patent Applications: Ser. No. 62/042,559, filed Aug. 27, 2014; Ser. No. 62/001,928, filed May 22, 2014; and Ser. No. 61/892,132, filed Oct. 17, 2013, the entire disclosures of these applications are hereby expressly incorporated by reference into this application.

TECHNICAL FIELD

This application relates to efficient and economical synthetic chemical processes for the preparation of pesticidal thioether and pesticidal sulfoxides. Further, the present application relates to certain novel compounds necessary for their synthesis. It would be advantageous to produce pesticidal thioether and pesticidal sulfoxides efficiently and in high yield from commercially available starting materials.

DETAILED DESCRIPTION

The following definitions apply to the terms as used throughout this specification, unless otherwise limited in specific instances.

As used herein, the term "alkyl" denotes branched or unbranched hydrocarbon chains.

Unless otherwise indicated, the term "cycloalkyl" as employed herein alone is a saturated cyclic hydrocarbon group, such as cyclopropyl, cyclobutyl, cyclopentyl, cyclohexyl.

The term "thio" as used herein as part of another group refers to a sulfur atom serving as a linker between two groups.

The term "halogen" or "halo" as used herein alone or as part of another group refers to chlorine, bromine, fluorine, and iodine.

The compounds and process of the present application are described in detail below.

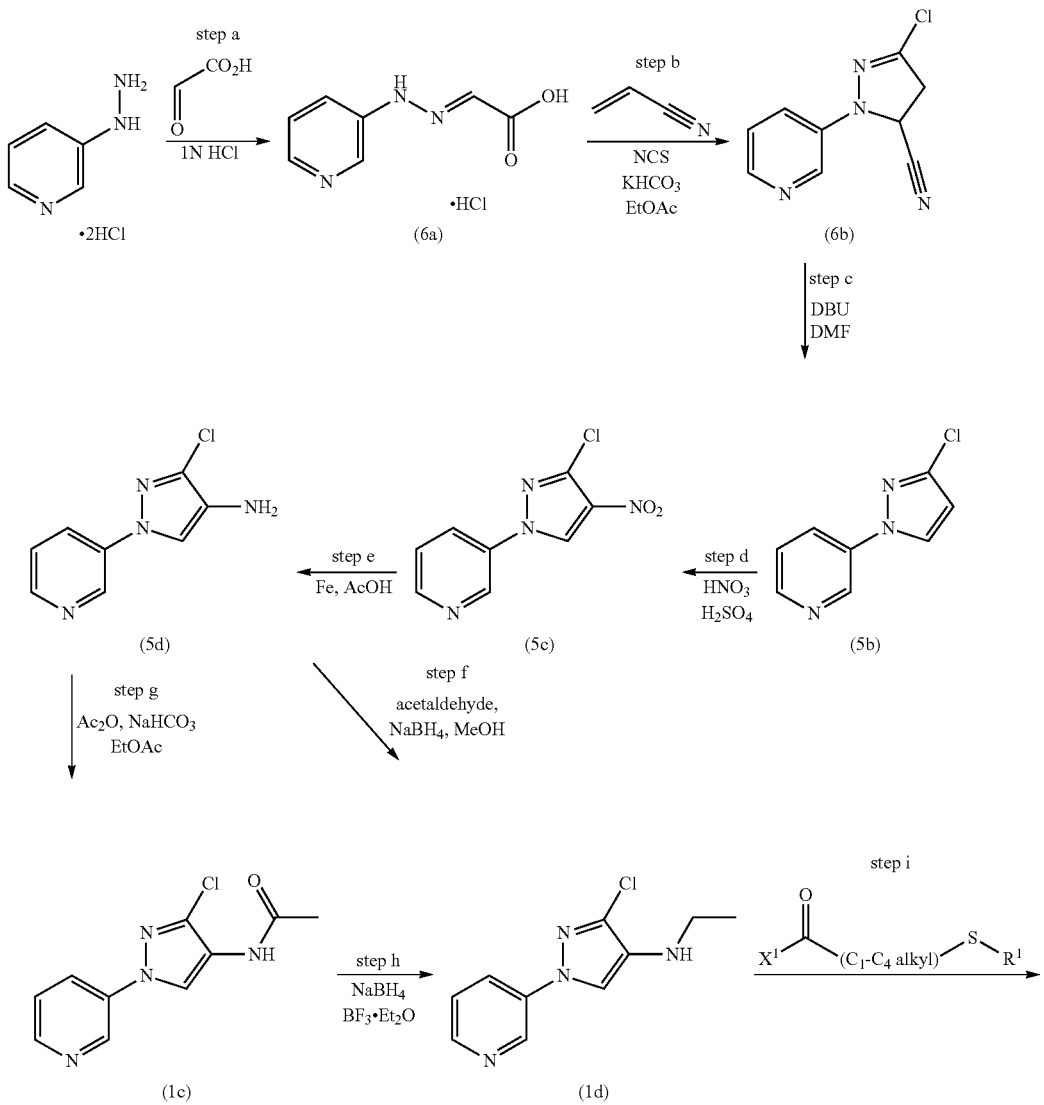

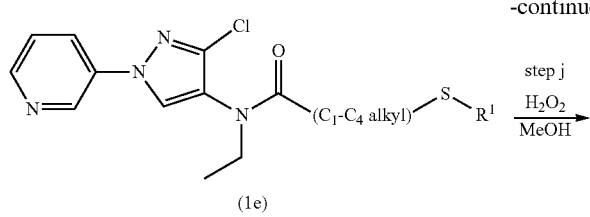

(1e)

step j
H₂O₂
MeOH

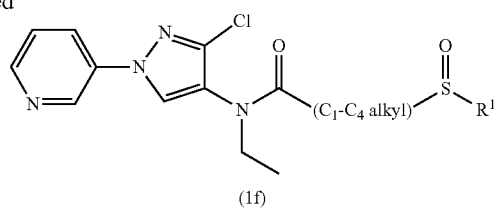

(1f)

In step a of Scheme 1, 3-hydrazinopyridine dihydrochloride is reacted with glyoxylic acid to yield (E)-2-(2-(pyridin-3-yl)hydrazono)acetic acid (6a). The reaction can be done with or without an acid, it is preferred, however, that an acid is used. For example, it is preferred that hydrochloric acid (HCl) is used. This reaction may be conducted in a protic solvent, for example, water. This reaction may be conducted at temperatures from about 0° C. to about 30° C.

In step b of Scheme 1, compound (6a) is reacted with acrylonitrile and a source of chlorine to yield 3-chloro-1-(pyridin-3-yl)-4,5-dihydro-1H-pyrazole-5-carbonitrile (6b). The chlorine source may be, for example, N-chlorosuccinimide (NCS). The reaction is also conducted in the presence of an inorganic base, preferably metal carbonates, metal hydroxides, metal phosphates, or metal hydrides, more preferably, potassium bicarbonate ($KHCO_3$). The reaction is also conducted in a polar aprotic solvent, preferably, ethyl acetate (EtOAc). This reaction may be conducted at temperatures from about −10° C. to about 30° C.

In step c of Scheme 1, compound (6b) undergoes dehydrocyanation to yield 3-(3-chloro-1H-pyrazol-1-yl)pyridine (5b). This reaction is conducted in the presence of an organic or inorganic base that promotes the dehydrocyanation, such as, 1,8-diazabicyclo-[5.4.0]undec-7-ene (DBU), 1,5-diazabicyclo[4.3.0]non-5-ene (DBN), or potassium hydroxide. The reaction may be conducted in a polar solvent, such as N,N-dimethyl-formamide (DMF), ethanol (EtOH), or tetrahydrofuran (THF). This reaction may be conducted at temperatures from about −10° C. to about 30° C.

In step d of Scheme 1, compound (5b) is nitrated with nitric acid ($HNO_3$), preferably in the presence of sulfuric acid ($H_2SO_4$) to yield 3-(3-chloro-4-nitro-1H-pyrazol-1-yl)pyridine (5c). The nitration may be conducted at temperatures from about −10° C. to about 30° C.

In step e of Scheme 1, compound (5c) is reduced to yield 3-chloro-1-(pyridin-3-yl)-1H-pyrazol-4-amine (5d). For example, compound (5c) may be reduced with iron in acetic acid (AcOH). Compound (5c) may also be reduced with iron and ammonium chloride ($NH_4Cl$). Alternatively, this reduction may be carried out using other techniques in the art, for example, compound (5c) may be reduced using palladium on carbon in the presence of hydrogen ($H_2$). This reaction may be conducted at temperatures from about −10° C. to about 30° C.

In step g of Scheme 1, 3-chloro-1-(pyridin-3-yl)-1H-pyrazol-4-amine (5d) is acylated with acetylating agents such as acetyl chloride or acetic anhydride, preferably acetic anhydride ($Ac_2O$) to yield N-(3-chloro-1-(pyridin-3-yl)-1H-pyrazol-4-yl)acetamide (1c). The acylation is conducted in the presence of a base, preferably an inorganic base, such as, sodium bicarbonate ($NaHCO_3$), and preferably, a polar solvent, such as ethyl acetate and/or tetrahydrofuran. This reaction may be conducted at temperatures from about −10° C. to about 30° C.

In step h of Scheme 1, N-(3-chloro-1-(pyridin-3-yl)-1H-pyrazol-4-yl)acetamide (1c) is reduced to yield 3-chloro-N-ethyl-1-(pyridin-3-yl)-1H-pyrazol-amine (1d). The reaction is conducted in the presence of a hydride source, preferably sodium borohydride ($NaBH_4$), and an acid source, such as a BrØnsted acid or a Lewis acid, preferably a Lewis acid, preferably borontrifluoride etherate ($BF_3.Et_2O$). It has been surprisingly discovered that the yield of the reaction is affected by the quality of the borontrifluoride etherate (purchased from different suppliers, currently, Sigma Aldrich product number 175501 being preferred). This reaction may be conducted at temperatures from about −10° C. to about 70° C.

Alternatively, instead of steps g and h, in step f of Scheme 1, 3-chloro-1-(pyridin-3-yl)-1H-pyrazol-4-amine (5d) is condensed with acetaldehyde followed by reduction of the imine intermediate to yield 3-chloro-N-ethyl-1-(pyridin-3-yl)-1H-pyrazol-4-amine (1d). The reaction may be conducted with a hydride source such as sodium borohydride in a polar protic solvent, such as methanol (MeOH) at temperatures from about −10° C. to about 40° C.

In step i of Scheme 1, 3-chloro-N-ethyl-1-(pyridin-3-yl)-1H-pyrazol-amine (1d) is reacted with an activated carbonyl thioether, indicated as $X^1C(=O)C_1-C_4$-alkyl-S—$R^1$, to yield pesticidal thioether (1e). $R^1$ is selected from the group consisting of $C_1-C_4$-haloalkyl and $C_1-C_4$-alkyl-$C_3-C_6$-halocycloalkyl, preferably, $R^1$ is selected from $CH_2CH_2CF_3$ or $CH_2$ (2,2-difluorocyclopropyl). $X^1$ is selected from Cl, $OC(=O)$ $C_1-C_4$ alkyl, or a group that forms an activated carboxylic acid. When $X^1$ is Cl or $OC(=O)C_1-C_4$ alkyl the reaction may be conducted in the presence of a base preferably, sodium bicarbonate to yield pesticidal thioether (1e). When $X^1$ is Cl or $OC(=O)C_1-C_4$ alkyl the reaction may also be conducted in the absence of a base to yield pesticidal thioether (1e). Alternatively, the reaction may be accomplished when $X^1C(=O)$ $C_1-C_4$-alkyl-S—$R^1$ is an activated carboxylic acid activated by such reagents as 2,4,6-tripropyl-trioxatriphosphinane-2,4,-trioxide ($T_3P^3$), carbonyldiimidazole (CDI), dicyclohexylcarbodiimide (DCC) or 1-ethyl-3-(3-dimethylaminopropyl) carbodiimide (EDC), preferably 2,4,6-tripropyl-trioxatriphosphinane-2,4,-trioxide and carbonyldiimidazole at temperatures from about 0° C. to about 80° C.; this reaction may also be facilitated with uronium or phosphonium activating groups such as O-(7-azabenzotriazol-1-yl)-N,N,N',N'-tetramethyluronium hexafluorophosphate (HATU) or benzotriazol-1-yl-oxytripyrrolidinophosphonium hexafluorophosphate (PyBOP), in the presence of an amine base such as diisopropylethylamine (DIPEA) or triethylamine (TEA) in an polar aprotic solvent such as N,N-dimethylformamide, tetrahydrofuran or dichloromethane ($CH_2Cl_2$), at temperatures from about −10° C. to about 30° C. to form pesticidal thioethers (1e). Activated carbonyl thioethers, may be prepared from $X^1C(=O)C_1-C_4$-alkyl-S—$R^1$, wherein $X^1$ is OH may be prepared by reacting the corresponding ester thioether, indicated as $X^1C(=O)C_1-C_4$-alkyl-S—$R^1$ wherein $X^1$ is $OC_1-C_4$-alkyl, with a metal hydroxide such as lithium hydroxide (LiOH) in a polar solvent such as methanol or tetrahydrofuran.

Alternatively, $X^1C(=O)C_1$-$C_4$-alkyl-S—$R^1$, wherein $X^1$ is OH or $OC_1$-$C_4$-alkyl may be prepared by the photochemical free-radical coupling of 3-mercaptopropionic acid and esters thereof with 3,3,3-trifluoropropene in the presence of 2,2-dimethoxy-2-phenylacetophenone initiator and long wavelength UV light in an inert organic solvent. While stoichiometric amounts of 3-mercaptopropionic acid or esters thereof and 3,3,3-trifluoropropene are required, because of its low boiling point, excess 3,3,3-trifluoropropene is usually employed to compensate for routine losses. From about 1 to about 10 mole percent initiator, 2,2-dimethoxy-2-phenyl-acetophenone, is typically used, with about 5 mole percent being preferred. Long wavelength UV light is sometimes called "black light" and ranges from about 400 to about 365 nanometers. The photochemical coupling is conducted in an inert organic solvent. Typical inert organic solvents must remain liquid to about −50° C., must remain relatively inert to the free radical conditions and must dissolve the reactants at reaction temperatures. Preferred inert organic solvents are aromatic and aliphatic hydrocarbons like toluene. The temperature at which the reaction is conducted is not critical but usually is from about −50° C. to about 35° C. Lower temperatures, however, are better for increased selectivity. Initially, it is important to keep the temperature below the boiling point of 3,3,3-trifluoropropene, i.e., about −18 to about −16° C. In a typical reaction, the inert organic solvent is cooled to less than about −50° C. and the 3,3,3-trifluoropropene is bubbled into the solvent. The 3-mercaptopropionic acid or esters thereof and 2,2-dimethoxy-2-phenylacetophenone are added and a long wave function (366 nm) UVP lamp (4 watt) is turned on. After sufficient conversion of 3-mercapto-propionic acid or esters thereof, the light is turned off and the solvent removed.

3-((3,3,3-Trifluoropropyl)thio)propanoic acid may also be prepared by the low temperature free-radical initiated coupling of 3-mercaptopropionic acid with 3,3,3-trifluoropropene in the presence of 2,2'-azobis(4-methoxy-2,4-dimethyl) valeronitrile (V-70) initiator at temperatures of about −50° C. to about 40° C. in an inert organic solvent. While stoichiometric amounts of 3-mercaptopropionic acid and 3,3,3-trifluoropropene are required, because of its low boiling point, excess 3,3,3-trifluoropropene is usually employed to compensate for routine losses. From about 1 to about 10 mole percent initiator, V-70, is typically used, with about 5 mole percent being preferred. The low temperature free-radical initiated coupling is conducted in an inert organic solvent. Typical inert organic solvents must remain liquid to about −50° C., must remain relatively inert to the free radical conditions and must dissolve the reactants at reaction temperatures. Preferred inert organic solvents are toluene, ethyl acetate, and methanol. The temperature at which the reaction is conducted from about −50° C. to about 40° C. Initially, it is important to keep the temperature below the boiling point of 3,3,3-trifluoropropene, i.e., about −18 to about −16° C. The solution is cooled to less than about −50° C. and the 3,3,3-trifluoropropene is transferred into the reaction mixture. After stirring at room temperature for 24 hours, the reaction mixture is heated to about 50° C. for about 1 hour to decompose any remaining V-70 initiator followed by cooling and solvent removal.

In step j of Scheme 1, thioether (1e) is oxidized with hydrogen peroxide ($H_2O_2$) in methanol to yield pesticidal sulfoxides (1f).

3-(3-Chloro-1H-pyrazol-1-yl)pyridine (5b) may alternatively be prepared through the reaction pathway disclosed in Scheme 2.

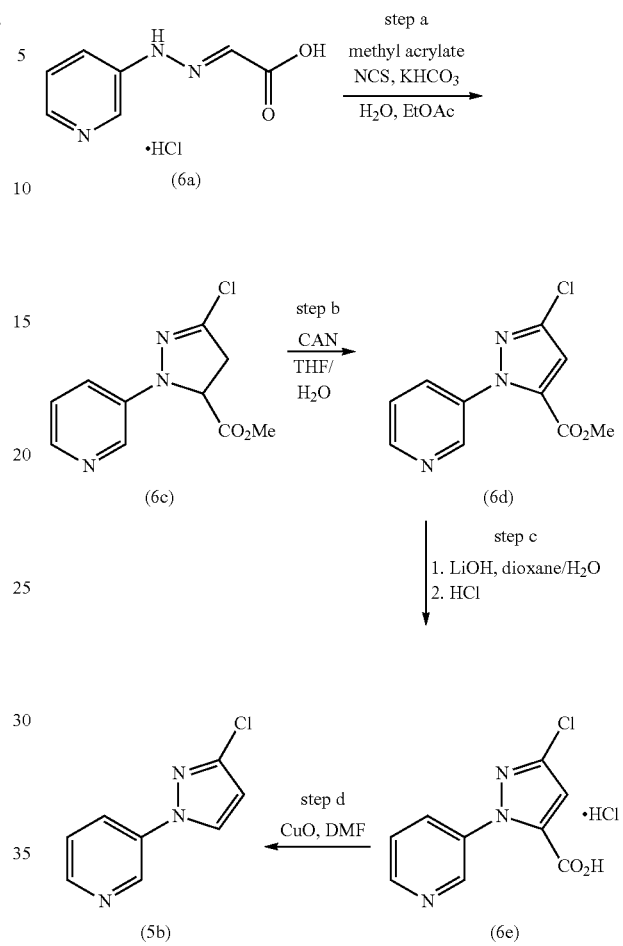

In step a of Scheme 2, (E)-2-(2-(pyridin-3-yl)hydrazono) acetic acid (6a) is reacted with methyl acrylate in the presence of a chlorine source such N-chlorosuccinimide, an inorganic base, preferably metal carbonates, metal hydroxides, metal phosphates, or metal hydrides, more preferably potassium bicarbonate and a polar aprotic solvent, preferably, ethyl acetate, and addition of a sub-stoichiometric amount of water to yield methyl 3-chloro-1-(pyridin-3-yl)-4,5-dihydro-1H-pyrazole-5-carboxylate (6c). This reaction may be conducted at temperatures from about −10° C. to about 30° C.

In step b of Scheme 2, methyl 3-chloro-1-(pyridin-3-yl)-4,5-dihydro-1H-pyrazole-5-carboxylate (6c) is oxidized with diammonium cerium (IV) nitrate (CAN) in water and polar solvents such as tetrahydrofuran at temperatures from about 0° C. to about 30° C. to yield methyl 3-chloro-1-(pyridin-3-yl)-1H-pyrazole-5-carboxylate (6d). It was surprisingly discovered that the oxidation in step b can also proceed with potassium permanganate ($KMnO_4$) as the oxidant in polar solvents such as acetone at temperatures from about 0° C. to about 30° C. However, many standard oxidation procedures such as, for example potassium persulfate ($K_2S_2O_8$), iodine pentoxide ($I_2O_5$), copper oxide (CuO), and hydrogen peroxide were found to be inoperative.

In step c of Scheme 2, methyl 3-chloro-1-(pyridin-3-yl)-1H-pyrazole-5-carboxylate (6d) is saponified in the presence of an inorganic base, preferably metal hydroxides or their hydrates such as lithium hydroxide hydrate ($LiOH·H_2O$) in water and a polar solvent such as dioxane at temperatures from about 0° C. to about 30° C. to yield 3-chloro-1-(pyridin-3-yl)-1H-pyrazole-5-carboxylic acid (6e). Alternatively, this process can also be accomplished by hydrolysis by exposing methyl 3-chloro-1-(pyridin-3-yl)-1H-pyrazole-5-carboxylate (6d) to a concentrated acid such as hydrochloric acid in water at temperatures from about 30° C. to about 100° C.

In step d of Scheme 2, 3-chloro-1-(pyridin-3-yl)-1H-pyrazole-5-carboxylic acid (6e) is decarboxylated in the presence of copper (II) oxide in polar solvents such as N,N-dimethylformamide at temperatures from about 80° C. to about 140° C. to yield 3-(3-chloro-1H-pyrazol-1-yl)pyridine (5b). It was surprisingly discovered that this decarboxylation only occurs in the presence of copper (II) oxide. Several known decarboxylation agents from the literature such as, for example, hydrochloric acid (See alternate synthetic route, Example 14), sulfuric acid, and palladium (II) trifluoroacetate/trifluoroacetic acid (Pd(TFA)$_2$/TFA) (See "CE-5") did not yield the desired product.

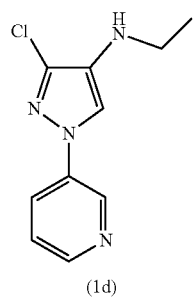

(1d)

3-Chloro-N-ethyl-1-(pyridin-3-yl)-1H-pyrazol-amine (1d) may be prepared through the reaction pathway sequence disclosed in Scheme 3. In step d1, N-(3-chlorol-(pyridin-3-yl)-1H-pyrazol-4-yl)acetamide (1c) may be alkylated with ethyl bromide (EtBr) in the presence of a base, such as sodium hydride (NaH), sodium tert-butoxide (NaOt-Bu), potassium tert-butoxide (KOt-Bu), or sodium tert-amyloxide, in a polar aprotic solvent, such as tetrahydrofuran, at temperatures from about 20° C. to about 40° C., over a period of time of about 60 hours to about 168 hours, to yield N-(3-chloro-1-(pyridin-3-yl)-1H-pyrazol-4-yl)-N-ethylacetamide (1c'). It has been discovered that use of an iodide additive, such as potassium iodide (KI) or tetrabutylammonium iodide (TBAI) can decrease the time necessary for the reaction to occur to about 24 hours. It has also been discovered that heating the reaction at about 50° C. to about 70° C. in a sealed reactor (to prevent loss of ethyl bromide) also decreases the reaction time to about 24 hours. In step d2, N-(3-chloro-1-(pyridin-3-yl)-1H-pyrazol-4-yl)-N-ethylacetamide (1c') may be treated with hydrochloric acid in water at temperatures from about 50° C. to about 90° C., to yield 3-chloro-N-ethyl-1-(pyridin-3-yl)-1H-pyrazol-amine (1d). The reaction pathway sequence disclosed in Scheme 3 may also be performed without the isolation of N-(3-chloro-1-(pyridin-3-yl)-1H-pyrazol-4-yl)-N-ethylacetamide (1c').

Scheme 3

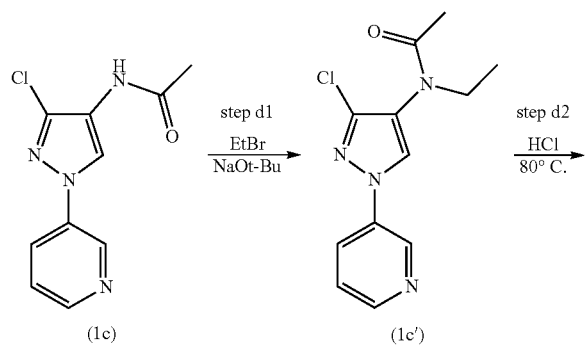

Scheme 4

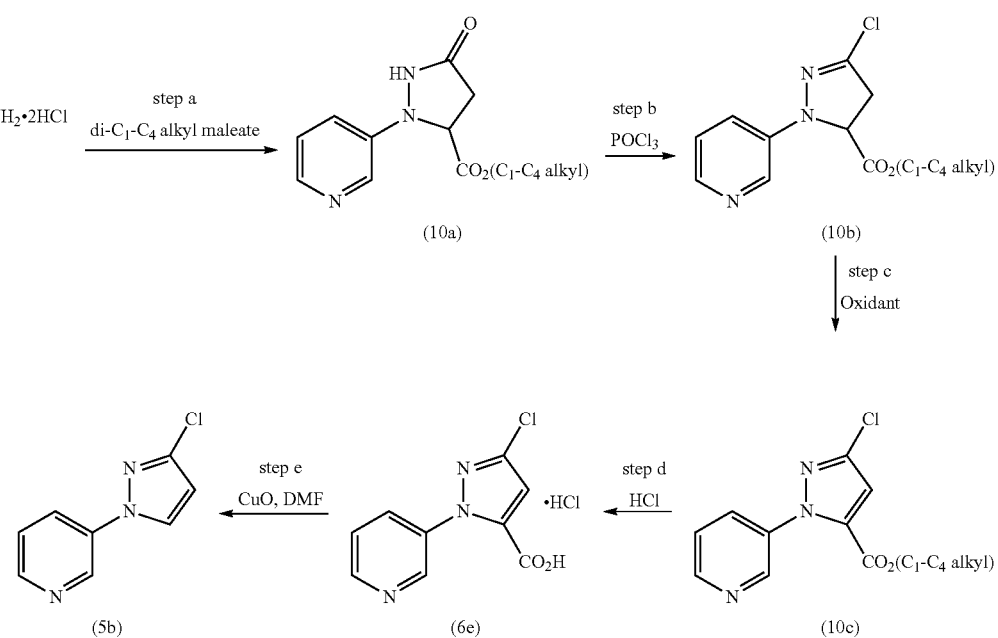

In step a of Scheme 4, 3-hydrazinopyridine.dihydrochloride is treated with a di-$C_1$-$C_4$ alkyl maleate such as diethyl maleate in a $C_1$-$C_4$ aliphatic alcohol at a temperature of about 25° C. to about 100° C. in the presence of an alkali metal $C_1$-$C_4$ alkoxide to provide pyrazolidine carboxylate (10a). While stoichiometric amounts of 3-hydrazinopyridine.-dihydrochloride and di-$C_1$-$C_4$ alkyl maleate are required, it is often convenient to use about a 1.5 fold to about a 2 fold excess of di-$C_1$-$C_4$ alkyl maleate. The cyclization is run in the presence of an alkali metal $C_1$-$C_4$ alkoxide base such as sodium ethoxide. It is often convenient to use about a 2 fold to about a 5 fold excess of base. The cyclization is performed in a $C_1$-$C_4$ aliphatic alcohol such as ethanol. It is most convenient that the alkoxide base and the alcohol solvent be the same, for example, sodium ethoxide in ethanol.

In step b of Scheme 4, the pyrazolidine carboxylate (10a) may be treated with a chlorinating reagent in an inert organic solvent at a temperature of about 25° C. to about 100° C. to provide chlorinated dihydropyrazole carboxylate (10b). Suitable chlorinating reagents include phosphoryl trichloride and phosphorus pentachloride. Phosphoryl trichloride is preferred. It is often convenient to use about a 1.1 fold to about a 10 fold excess of the chlorinating reagent. The chlorination is performed in an organic solvent that is inert to the chlorinating reagent. Suitable solvents include nitriles such as acetonitrile. With phosphoryl trichloride as the chlorinating reagent, acetonitrile is a preferred solvent.

In step c of Scheme 4, chlorinated dihydropyrazole carboxylate (10b) may treated with an oxidant in an organic solvent at a temperature of about 25° C. to about 100° C. to provide chlorinated pyrazole carboxylate (10c). Suitable oxidants include manganese (IV) oxide and sodium persulfate/sulfuric acid. It is often convenient to use about a 1.5 fold to about a 15 fold excess of oxidant. The oxidation is performed in an organic solvent that is inert to the oxidant. Suitable solvents include nitriles such as acetonitrile. With manganese (IV) oxide ($MnO_2$) or sodium persulfate/sulfuric acid as the oxidant, acetonitrile is a preferred solvent.

In step d of Scheme 4, chlorinated pyrazole carboxylate (10c) may then be converted to the desired 3-chloro-1-(pyridin-3-yl)-1H-pyrazole-5-carboxylic acid hydrochloride (6e) by treatment in aqueous hydrochloric acid at a temperature of about 25° C. to about 100° C. While stoichiometric amounts of reagents are required, it is often convenient to use an excess of reagents with respect to the chlorinated pyrazole carboxylate. Thus, aqueous hydrochloric acid is used in large excess as the reaction medium. Alternatively, chlorinated pyrazole carboxylates may be saponified in the presence of an inorganic base, preferably metal hydroxides or their hydrates such as lithium hydroxide hydrate ($LiOH·H_2O$) in water and a polar solvent such as dioxane at temperatures from about 0° C. to about 30° C. to yield 3-chloro-1-(pyridin-3-yl)-1H-pyrazole-5-carboxylic acid (6e).

In step e of Scheme 4, 3-chloro-1-(pyridin-3-yl)-1H-pyrazole-5-carboxylic acid hydrochloride (6e) is decarboxylated in the presence of copper (II) oxide in polar solvents such as N,N-dimethylformamide at temperatures from about 80° C. to about 140° C. to yield 3-(3-chloro-1H-pyrazol-1-yl)pyridine (5b). It was surprisingly discovered that this decarboxylation only occurs in the presence of copper (II) oxide. Several known decarboxylation agents from the literature such as, for example, hydrochloric acid (See alternate synthetic route, Example 14), sulfuric acid, and palladium (II) trifluoroacetate/trifluoroacetic acid (See "CE-5") did not yield the desired product.

EXAMPLES

The following examples are presented to better illustrate the processes of the present application.

Compound Examples

Example 1

(E)-2-((2-Pyridin-3-yl)hydrazono)acetic acid hydrochloride (6a)

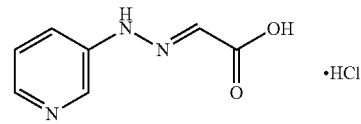 [SMILES: O=C(O)/C=N/Nc1cccnc1 ; Cl]

Glyoxylic acid (50% in water) (54.5 mL, 494 mmol) and 1 N hydrochloric acid (~100 mL) were added to 3-hydrazinopyridine dihydrochloride (60.0 g, 330 mmol) and the reaction mixture was stirred at room temperature (about 22° C.) for 2 hours, at which point solid had started to precipitate. The reaction was stirred for 24 hours, at which point LC/MS indicated that it was complete. The mixture was transferred to a flask using acetonitrile (1 L). The mixture was azeotroped three times from acetonitrile (1 L). The resulting suspension was filtered to afford a green solid which was washed with acetonitrile and vacuum dried at 40° C. to afford the desired product (68.3 g, 98%): mp 173-174° C.; $^1$H NMR (400 MHz, DMSO-$d_6$) δ 12.55 (d, J=1.2 Hz, 1H), 8.61 (d, J=2.5 Hz, 1H), 8.40 (dt, J=5.4, 0.9 Hz, 1H), 8.14 (ddd. J=8.7, 2.6, 1.2 Hz, 1H), 7.91 (dd, J=8.7, 5.4 Hz, 1H), 7.43 (d, J=1.0 Hz, 1H); $^{13}$C NMR (101 MHz, DMSO) δ 164.29, 143.15, 133.15, 131.85, 127.97, 127.61, 126.30; ESIMS m/z 166 ([M+H]$^+$).

Example 2

3-Chloro-1-(pyridine-3-yl)-4,5-dihydro-1H-pyrazole-5-carbonitrile (6b)

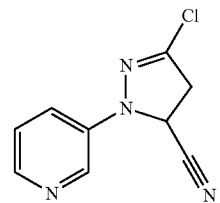 [SMILES: N#CC1CC(Cl)=NN1c1cccnc1]

(E)-2-((2-Pyridin-3-yl)hydrazono)acetic acid hydrochloride (2.00 g, 9.42 mmol) was stirred in ethyl acetate (47.1 mL). N-Chlorosuccinimide (2.36 g, 19.3 mmol), acrylonitrile (1.85 mL, 28.3 mmol) and potassium bicarbonate (2.86 g, 28.3 mmol) were added. Water (0.05 mL) was added and the mixture was stirred at room temperature for 18 hours. Saturated aqueous sodium chloride (brine, 50 mL) was added and the mixture was filtered through Celite®. The filter cake was washed with ethyl acetate (40 mL) and the layers were separated. The organic layers were combined, dried and concentrated to afford a residue. The resulting residue was purified by flash column chromatography using 80-100% ethyl acetate/hexanes as eluent to afford the desired product as an orange solid (1.40 g, 57.5%): $^1$H NMR (400 MHz, CDCl$_3$) δ 8.51 (dd, J=2.9, 0.7 Hz, 1H), 8.33 (dd, J=4.7, 1.4 Hz, 1H), 7.51 (ddd, J=8.4, 2.9, 1.4 Hz, 1H), 7.30 (ddd, J=8.5, 4.7, 0.8 Hz, 1H), 5.06 (dd, J=11.3, 5.9 Hz, 1H), 3.64 (dd, J=17.4, 11.3 Hz, 1H), 3.51 (dd, J=17.4, 5.9 Hz, 1H); $^{13}$C NMR (101 MHz, CDCl$_3$) δ 143.34, 142.79, 140.11, 136.16, 123.92, 121.93, 115.80, 51.39, 43.04; ESIMS m/z 207 ([M+H]$^+$).

Example 3

3-(3-Chloro-1H-pyrazol-1-yl)pyridine (5b)

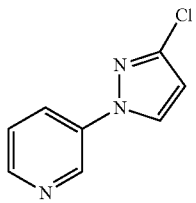 [SMILES: Clc1ccn(-c2cccnc2)n1]

3-Chloro-1-(pyridine-3-yl)-4,5-dihydro-1H-pyrazole-5-carbonitrile (0.500 g, 2.42 mmol) was stirred in N,N-dimethylformamide (6.05 mL). 1,8-Diazabicyclo[5.4.0]undec-7-ene (0.543 mL, 3.63 mmol) was added and the dark mixture was stirred at room temperature overnight. LC/MS analysis indicated that the reaction was complete. The mixture was concentrated and the dark oil was dissolved in ethyl acetate and washed with 15% aqueous lithium chloride (LiCl) and brine. The organic portion was dried over sodium sulfate (Na$_2$SO$_4$) and concentrated. The residue was purified by flash column chromatography using ethyl acetate. The pure fractions were concentrated and the residue was vacuum dried at 45° C. to yield the desired product as a white solid (450 mg, 93%): mp: 66-68° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (m, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.0.

Alternate Synthetic Route to:
3-(3-chloro-1H-pyrazol-1-yl)pyridine (Scheme 2)

3-Chloro-1-(pyridin-3-yl)-1H-pyrazole-5-carboxylic acid hydrochloride (1.00 g, 3.65 mmol) was stirred in N,N-dimethylformamide (10 mL). Copper(II) oxide (58.0 mg, 0.730 mmol) was added and the reaction was heated at 120° C. for 16 hours, at which point the reaction was ~20% complete. Additional copper(II) oxide (112 mg, 1.46 mmol) was added and the reaction was stirred for 5 hours, at which point the reaction was complete by thin layer chromatography (TLC) [Eluent: ethyl acetate]. The mixture was diluted with ammonium hydroxide (NH$_4$OH) and water and extracted with ethyl acetate. The organic layer was washed with 15% lithium chloride and concentrated to provide an orange solid. The residue was purified by flash column chromatography using ethyl acetate as eluent and the pure fractions were concentrated to afford the desired product as a white solid (481 mg, 69.7%). The spectral characterization was in agreement with the product prepared previously.

Example 4

3-(3-Chloro-4-nitro-1H-pyrazol-1-yl)pyridine (5c)

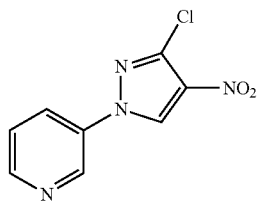

To a 100 mL round bottom flask was charged 3-(3-chloro-1H-pyrazol-1-yl)pyridine (2.0 g, 11 mmol) and concentrated sulfuric acid (4 mL). This suspension was cooled to ~5° C. and 2:1 (v/v) concentrated nitric acid/sulfuric acid (3 mL, prepared by adding the concentrated sulfuric acid to a stifling and cooling solution of the nitric acid) was added dropwise at a rate such that the internal temperature was maintained <15° C. The reaction was allowed to warm to 20° C. and stirred for 18 hours. A sample of the reaction mixture was carefully diluted into water, basified with 50% sodium hydroxide (NaOH) and extracted with ethyl acetate. Analysis of the organic layer indicated that the reaction was complete. The reaction mixture was carefully added to ice cold water (100 mL) at <20° C. and basified with 50% sodium hydroxide at <20° C. The resulting light yellow suspension was stirred for 2 hours and filtered. The filter cake was rinsed with water (3×20 mL) and dried to afford an off-white solid (2.5 g, quantitative): mp 141-143° C.; $^1$H NMR (400 MHz, DMSO-d$_6$) δ 9.86 (s, 1H), 9.23-9.06 (m, 1H), 8.75-8.60 (m, 1H), 8.33 (ddd, J=8.4, 2.8, 1.4 Hz, 1H), 7.64 (ddd, J=8.5, 4.7, 0.7 Hz, 1H); $^{13}$C NMR (101 MHz, DMSO-d$_6$) δ 149.49, 140.75, 136.02, 134.43, 132.14, 131.76, 127.22, 124.31; EIMS m/z 224 ([M]$^+$).

Example 5

3-Chloro-1-(pyridin-3-yl)-1H-pyrazol-4-amine (5d)

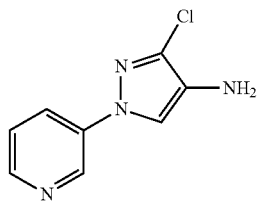 [SMILES: O=[N+]([O-])c1cn(-c2cccnc2)nc1Cl]

To a 100 mL, 3-neck round bottom flask was charged 3-(3-chloro-4-nitro-1H-pyrazol-1-yl)pyridine (2.40 g, 10.7 mmol), acetic acid (4 mL), ethanol (4.8 mL) and water (4.8 mL). The mixture was cooled to 5° C. and iron powder (2.98 g, 53.4 mmol) was added portionwise over ~15 minutes. The reaction was allowed to stir at 20° C. for 18 hours and diluted to 50 mL with water. The mixture was filtered through Celite® and the filtrate was carefully basified with 50% sodium hydroxide solution. The resulting suspension was filtered through Celite® and the filtrate was extracted with ethyl acetate (3×20 mL). The organics were dried over sodium sulfate and concentrated to dryness to afford a tan colored solid, which was further dried under vacuum for 18 hours (2.2 g, quantitative): mp 145-147° C.; $^1$H NMR (400 MHz, DMSO-d$_6$) δ 8.95 (dd, J=2.6, 0.8 Hz, 1H), 8.45 (dd, J=4.7, 1.4 Hz, 1H), 8.08 (ddd, J=8.4, 2.7, 1.4 Hz, 1H), 7.91 (s, 1H), 7.49 (ddd, J=8.3, 4.7, 0.8 Hz, 1H), 4.43 (s, 2H); $^{13}$C NMR (101 MHz, DMSO-d$_6$) δ 146.35, 138.53, 135.72, 132.09, 130.09, 124.29, 124.11, 114.09; EIMS m/z 194 ([M]$^+$).

Alternate Synthetic Route to:
3-Chloro-1(pyridin-3-yl)-1H-pyrazol-4-amine

A suspension of 3-(3-chloro-4-nitro-1H-pyrazol-1-yl)pyridine (1.00 g, 4.45 mmol) and palladium on carbon (10 wt %, 0.05 g, 0.467 mmol) in methanol (20 mL) was purged with nitrogen (N$_2$) three times, followed by hydrogen three times. The reaction was stirred at 20° C. under 40 psi of hydrogen for 4 hours. After which time the reaction was purged with nitrogen three times and analyzed by thin layer chromatography [Eluent: 10% methanol/dichloromethane], which indicated that the reaction was complete. The reaction mixture was filtered through a Celite® pad and the pad was rinsed with methanol (2×10 mL). The filtrates were concentrated to dryness to afford a slightly pink solid (0.82 g, 95%). The spectral characterization was in agreement with the product prepared previously.

Alternate Synthetic Route to: 3-(3-chloro-4-amino-1H-pyrazol-1-yl)pyridine (5d)

In a 250 mL 3-neck round bottom flask was added 3-(3-chloro-4-nitro-1H-pyrazol-1-yl)pyridine (5.00 g, 21.8 mmol), ethanol (80 mL), water (40 mL), and ammonium chloride (5.84 g, 109 mmol). The suspension was stirred under nitrogen stream for 5 minutes then iron powder (4.87 g, 87.2 mmol) added. The reaction mixture was heated to reflux (~80° C.) and held there for 4 hours. After 4 hours a reaction aliquot taken showed by HPLC analysis the reaction had gone to full conversion. Ethyl acetate (120 mL) and Celite® (10 g) were added to the reaction mixture and let stir for 10 minutes. The black colored suspension was then filtered via a Celite® pad and the pad rinsed with ethyl acetate (80 mL). The reaction mixture was washed with saturated sodium bicarbonate (30 mL) and the organic layer was assayed. The assay gave (4.19 g, 99%) of product. The organic solvent was removed in vacuo to give a brown colored crude solid that was used without further purification.

Example 6

N-(3-Chloro-1-(pyridin-3-yl)-1H-pyrazol-4-yl)acetamide (1c)

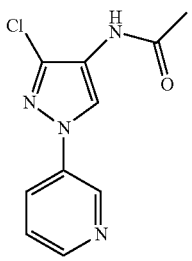 [SMILES: CC(=O)Nc1cn(-c2cccnc2)nc1Cl]

A 100 mL three-neck round bottom flask was charged with 3-chloro-1(pyridin-3-yl)-1H-pyrazol-4-amine (1.00 g, 5.14 mmol) and ethyl acetate (10 mL). sodium bicarbonate (1.08 g, 12.9 mmol) was added, followed by dropwise addition of acetic anhydride (0.629 g, 6.17 mmol) at <20° C. The reaction was stirred at 20° C. for 2 hours to afford a suspension, at which point thin layer chromatography analysis [Eluent: ethyl acetate] indicated that the reaction was complete. The reaction was diluted with water (50 mL) and the resulting suspension was filtered. The solid was rinsed with water (10 mL) followed by methanol (5 mL). The solid was further dried under vacuum at 20° C. to afford the desired product as a white solid (0.804 g, 66%): mp 169-172° C.; $^1$H NMR (400 MHz, DMSO-d$_6$) δ 9.84 (s, 1H), 9.05 (dd, J=2.8, 0.8 Hz, 1H), 8.82 (s, 1H), 8.54 (dd, J=4.7, 1.4 Hz, 1H), 8.20 (ddd, J=8.4, 2.8, 1.4 Hz, 1H), 7.54, (ddd, J=8.3, 4.7, 0.8 Hz, 1H), 2.11 (s, 3H); $^{13}$C NMR (101 MHz, DMSO-d$_6$) δ 168.12, 147.46, 139.42, 135.46, 133.60, 125.47, 124.21, 122.21, 120.16, 22.62; EIMS m/z 236 ([M]$^+$).

Example 7

3-Chloro-N-ethyl-1-(pyridin-3-yl)-1H-pyrazol-4-amine (1d)

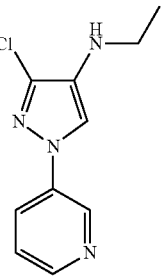

A 100 mL 3-neck round bottom flask was charged with N-(3-chloro-1-(pyridin-3-yl)-1H-pyrazol-4-yl)acetamide (475 mg, 2.01 mmol) and tetrahydrofuran (10 mL). borontrifluoride etherate (0.63 mL, 5.02 mmol) was added and the mixture was stirred for 15 minutes to give a suspension. Sodium borohydride (228 mg, 6.02 mmol) was added and the reaction was heated at 60° C. for 4 hours, at which point thin layer chromatography analysis [Eluent: ethyl acetate, sample was prepared by treatment of reaction mixture with hydrochloric acid, followed by sodium bicarbonate basification and ethyl acetate extraction] indicated that the reaction was complete. Water (10 mL) and concentrated hydrochloric acid (1 mL) were added and the reaction was heated at 60° C. for 1 hour. The reaction mixture was cooled to room temperature and distilled to remove tetrahydrofuran. The mixture was neutralized with saturated aqueous sodium bicarbonate to pH~8 to afford a suspension, which was stirred for 1 hour and filtered. The filter cake was rinsed with water (10 mL) and dried under vacuum to afford a white solid (352 mg, 79%): mp 93-96° C.; $^1$H NMR (400 MHz, DMSO-d$_6$) δ 8.99 (d, J=2.7 Hz, 1H), 8.44 (dd, J=4.6, 1.4 Hz, 1H), 8.10 (ddd, J=8.4, 2.7, 1.4 Hz, 1H), 8.06 (s, 1H), 7.50 (dd, J=8.4, 4.7 Hz, 1H), 4.63 (t, J=6.0 Hz, 1H), 3.06-2.92 (m, 2H), 1.18 (t, J=7.1 Hz, 3H); $^{13}$C NMR (101 MHz, DMSO-d$_6$) δ 146.17, 138.31, 135.81, 132.82, 130.84, 124.10, 123.96, 112.23, 40.51, 14.28; EIMS m/z 222 ([M]$^+$).

Alternate Synthetic Route to: 3-Chloro-N-ethyl-1-(pyridin-3-yl)-1H-pyrazol-4-amine (1d)

A 3-neck, 100 mL round bottom flask was charged with 3-chloro-1-(pyridin-3-yl)-1H-pyrazol-4-amine (5d) (500 mg, 2.57 mmol) and methanol (5 mL). The mixture was stirred for 5 minutes to give a clear solution. Acetaldehyde (136 mg, 3.09 mmol) was added and the reaction was stirred at 20° C. for 6 hours. Sodium borohydride (194 mg, 5.14 mmol) was added and the reaction was stirred at 20° C. for 1 hour, at which point thin layer chromatography analysis [Eluent: ethyl acetate] indicated that some starting material remained and a major product formed. The reaction mixture was quenched with water (10 mL) and concentrated under reduced pressure to remove methanol. Ethyl acetate (10 mL) was added and the organic layer was concentrated to dryness. The residue was purified by flash column chromatography using 20-40% ethyl acetate/hexanes as eluent. The fractions containing pure product were combined and concentrated to afford a white solid (328 mg, 58%). The spectral characterization was in agreement with the product prepared previously.

Alternate Synthetic Route to: 3-Chloro-N-ethyl-1-(pyridin-3-yl)-1H-pyrazol-amine

Step 1. N-(3-Chloro-1-(pyridin-3-yl)-1H-pyrazol-4-yl)-N-ethylacetamide (1c')

To a 3-neck, 100-mL round bottom flask was charged N-(3-chloro-1-(pyridin-3-yl)-1H-pyrazol-4-yl)acetamide (5.00 g, 21.1 mmol) and tetrahydrofuran (50 mL). Sodium tert-butoxide (3.05 g, 31.7 mmol) was added (causing a temperature rise from 22° C. to 27.9° C.), followed by bromoethane (4.70 mL, 63.4 mmol). The reaction was stirred at 35° C. for 168 hours, at which point HPLC analysis indicated that only 2.9% (area under the curve, AUC) starting material remained. The reaction mixture was concentrated to give a brown residue, which was diluted with ethyl acetate (50 mL) and water (50 mL). The aqueous layer was extracted with ethyl acetate (4×50 mL) and the combined organics were concentrated to give a brown residue. The residue was dissolved in dichloromethane (2×10 mL) and purified by flash column chromatography using 60-100% ethyl acetate/hexanes as eluent. The fractions containing pure product were combined and concentrated to afford the title product as a yellow solid (4.20 g, 74%): $^1$H NMR (400 MHz, CDCl$_3$) δ 8.98 (d, J=2.7, 0.8 Hz, 1H), 8.62 (dd, J=4.8, 1.4 Hz, 1H), 8.06 (ddd, J=8.3, 2.7, 1.4 Hz, 1H), 8.00 (s, 1H), 7.47 (dd, J=8.3, 4.7 Hz, 1H), 3.71 (q, J=7.1 Hz, 2H), 1.97 (s, 3H), 1.16 (t, J=7.2 Hz, 3H); $^{13}$C NMR (101 MHz, CDCl$_3$) δ 170.69, 148.56, 140.89, 139.95, 135.64, 126.22, 126.08, 124.86, 124.09, 43.77, 22.27, 13.15; mp: 87-91° C.; ESIMS m/z 265 ([M+H]$^+$).

Step 1. N-(3-Chloro-1-(pyridin-3-yl)-1H-pyrazol-4-yl)-N-ethylacetamide (1c')

To a 3-neck, 100-mL round bottom flask was charged N-(3-chloro-1-(pyridin-3-yl)-1H-pyrazol-4-yl)acetamide (1.66 g, 7.0 mmol) and tetrahydrofuran (16 mL). Sodium tert-butoxide (0.843 g, 8.77 mmol, 1.25 eq) and ethyl bromide (0.78 mL, 10.52 mmol, 1.5 eq) were added and the reactor was capped with a septa. The reaction was stirred at 58° C. for 24 hours, at which point HPLC analysis indicated that only 1.97% starting material remained. The mixture was concentrated to give a brown residue, which was dissolved in water (20 mL) and ethyl acetate (20 mL). The aqueous layer was extracted with ethyl acetate (2×20 mL) and the combined organics were concentrated to dryness. The residue was passed through a silica gel plug (40 g silica) and eluted with ethyl acetate (200 mL). The filtrates were concentrated to dryness and further dried under vacuum at 20° C. to afford a yellow solid (1.68 g, 89%). Characterization matched sample prepared by previous method.

Step 1. N-(3-Chloro-1-(pyridin-3-yl)-1H-pyrazol-4-yl)-N-ethylacetamide (1c')

In a 125 mL 3-neck round-bottomed flask was added N-(3-chloro-1-(pyridin-3-yl)-1H-pyrazol-4-yl)acetamide (2.57 g, 9.44 mmol), tetrahydrofuran (55 mL), and sodium tert-butoxide (1.81 g, 18.9 mmol). The suspension was stirred for 5 minutes then ethyl bromide (1.41 mL, 18.9 mmol), and tetrabutylammonium iodide (67 mg, 0.2 mmol) were added. The resulting gray colored suspension was then heated to 38° C. The reaction was analyzed after 3 hours and found to have gone to 81% completion, after 24 hours the reaction was found to have gone to completion. The reaction mixture was allowed to cool to ambient temperature and quenched with ammonium hydroxide/formic acid (HCO$_2$H) buffer (10 mL). The mixture was then diluted with tetrahydrofuran (40 mL), ethyl acetate (120 mL), and saturated sodium bicarbonate (30 mL). The layers were separated and the aqueous layer was extracted with ethyl acetate (2×30 mL). The organic layers were combined and silica gel (37 g) was added. The solvent was removed in vacuo to give a solid that was purified using semi-automated silica gel chromatography (RediSep Silica 220 g column; hexanes (0.2% triethylamine)/ethyl acetate, 40/60 to 0/100 gradient elution system, flow rate 150 mL/minutes) to give, after concentration, an orange solid weighing (2.19 g, 88%)

Step 2. 3-Chloro-N-ethyl-1-(pyridin-3-yl)-1H-pyrazol-amine (1d)

A solution of N-(3-chloro-1-(pyridin-3-yl)-1H-pyrazol-4-yl)-N-ethylacetamide (1.8 g, 6.80 mmol) in 1 N hydrochloric acid (34 mL) was heated at 80° C. for 18 hours, at which point HPLC analysis indicated that only 1.1% starting material remained. The reaction mixture was cooled to 20° C. and basified with 50 wt % sodium hydroxide to pH>9. The resulting suspension was stirred at 20° C. for 2 hours and filtered. The filter cake was rinsed with water (2×5 mL), conditioned for 30 minutes, and air-dried to afford an off-white solid (1.48 g, 95%): $^1$H NMR (400 MHz, DMSO-d6) δ 9.00 (dd, J=2.8, 0.8 Hz, 1H), 8.45 (dd, J=4.7, 1.4 Hz, 1H), 8.11 (ddd, J=8.4, 2.8, 1.4 Hz, 1H), 8.06 (d, J=0.6 Hz, 1H), 7.49 (ddd, J=8.4, 4.7, 0.8 Hz, 1H), 4.63 (t, J=6.0 Hz, 1H), 3.00 (qd, J=7.1, 5.8 Hz, 2H), 1.19 (t, J=7.1 Hz, 3H); $^{13}$C NMR (101 MHz, DMSO) δ 146.18, 138.31, 135.78, 132.82, 130.84, 124.08, 123.97, 112.23, 40.51, 14.28; ESIMS 223 ([M+H]$^+$).

Alternate Synthetic Route to: 3-Chloro-N-ethyl-1-(pyridin-3-yl)-1H-pyrazol-amine To a 3-neck, 100-mL round bottom flask was charged N-(3-chloro-1-(pyridin-3-yl)-1H-pyrazol-4-yl)acetamide (5 g, 21.13 mmol) and tetrahydrofuran (50 mL). Sodium tert-butoxide (4.06 g, 42.3 mmol) was added (causing a temperature rise from 22° C. to 27.6° C.), followed by ethyl bromide (6.26 mL, 85 mmol). The reaction was stirred at 35° C. for 144 h at which point only 3.2% (AUC) starting material remained. The reaction mixture was concentrated to give a brown residue, which was dissolved in 1N hydrochloric acid (106 mL, 106 mmol) and heated at 80° C. for 24 hours, at which point HPLC analysis indicated that the starting material had been consumed. The reaction was cooled to 20° C. and basified with 50% sodium hydroxide to pH>9. The resulting suspension was stirred at 20° C. for 1 hour and filtered, the filter cake was rinsed with water (25 mL) to afford a brown solid (5.18 g). The resulting crude product was dissolved in ethyl acetate and passed through a silica gel plug (50 g) using ethyl acetate (500 mL) as eluent. The filtrate was concentrated to dryness to afford a white solid (3.8 g, 80%).

Example 8

N-(3-Chloro-1-(pyridin-3-yl)-1H-pyrazol-4-yl)-N-ethyl-3-((3,3,3-trifluoropropyl)thio)propanamide (Compound 8.6)

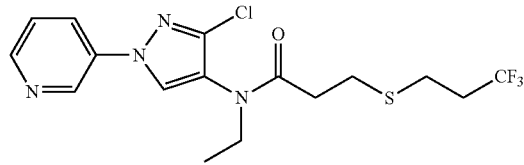 [SMILES: CCN(C(=O)CCSCCC(F)(F)F)c1cn(-c2cccnc2)nc1Cl]

A 100 mL three-neck round bottom flask was charged with 3-chloro-N-ethyl-1-(pyridine-3-yl)-1H-pyrazol-4-amine (5.00 g, 22.5 mmol) and ethyl acetate (50 mL). Sodium bicarbonate (4.72 g, 56.1 mmol) was added, followed by dropwise addition of 3-((3,3,3-trifluoropropyl)thio)propanoyl chloride (5.95 g, 26.9 mmol) at <20° C. for 2 hours, at which point HPLC analysis indicated that the reaction was complete. The reaction was diluted with water (50 mL) (off-gassing) and the layers separated. The aqueous layer was extracted with ethyl acetate (20 mL) and the combined organic layers were concentrated to dryness to afford a light brown solid (10.1 g, quantitative). A small sample of crude product was purified by flash column chromatography using ethyl acetate as eluent to obtain an analytical sample: mp 79-81° C.; $^1$H NMR (400 MHz, DMSO-$d_6$) δ 9.11 (d, J=2.7 Hz, 1H), 8.97 (s, 1H), 8.60 (dd, J=4.8, 1.4 Hz, 1H), 8.24 (ddd, J=8.4, 2.8, 1.4 Hz, 1H), 7.60 (ddd, J=8.4, 4.7, 0.8 Hz, 1H), 3.62 (q, J=7.2 Hz, 2H), 2.75 (t, J=7.0 Hz, 2H), 2.66-2.57 (m 2H), 2.57-2.44 (m, 2H), 2.41 (t, J=7.0 Hz, 2H), 1.08 (t, J=7.1 Hz, 3H). EIMS m/z 406 ([M]$^+$).

Alternate Synthetic Route to: N-(3-Chloro-1-(pyridin-3-yl)-1H-pyrazol-4-yl)-N-ethyl-3-((3,3,3-trifluoropropyl)thio)propanamide A 20 mL vial was charged with 3-((3,3,3-trifluropropyl) thio)propanoic acid (0.999 g, 4.94 mmol) and acetonitrile (5 mL). Carbonyldiimidazole (0.947 g, 5.84 mmol) (off-gassing) and 1H-imidazole hydrochloride (0.563 g, 5.39 mmol) were added and the reaction was stirred at 20° C. for 4 hours. 3-Chloro-N-ethyl-1-(pyridine-3-yl)-1H-pyrazol-amine (1.00 g, 4.49 mmol) was added and the reaction was stirred at 75° C. for 42 hours, at which point HPLC analysis indicated that the conversion was 96%. The reaction was cooled to 20° C. and concentrated to dryness. The residue was purified by flash column chromatography using 80% ethyl acetate/hexanes as eluent. Pure fractions were combined and concentrated to afford a light yellow solid (1.58 g, 86%).

Alternate Synthetic Route to: N-(3-Chloro-1-(pyridin-3-yl)-1H-pyrazol-4-yl)-N-ethyl-3-((3,3,3-trifluoropropyl)thio)propanamide A solution of 3-((3,3,3-trifluoropropyl)thio)propanoic acid (2.18 g, 10.8 mmol) and 3-chloro-N-ethyl-1-(pyridine-3-yl)-1H-pyrazol-amine (2.00 g, 8.98 mmol) in ethyl acetate (16 mL) was cooled to 5° C. Diisopropylethylamine (5.15 mL, 29.6 mmol) was added dropwise at 0-5° C. over 30 minutes, followed by the addition of 2,4,6-tripropyl-trioxatriphosphinane-2,4,-trioxide (4.00 g, 12.6 mmol) over 30 minutes at 0-5° C. The reaction was allowed to warm to 25-30° C. and stirred for 2 h. Upon reaction completion, the reaction mixture was cooled to 0-5° C. and quenched with water (12 mL). The layers were separated and the aqueous layer was extracted with ethyl acetate (30 mL). The combined organic layers were concentrated to afford the desired product as an oil (3.40 g, 94%).

Alternate Synthetic Route to: N-(3-Chloro-1-(pyridin-3-yl)-1H-pyrazol-4-yl)-N-ethyl-3-((3,3,3-trifluoropropyl)thio)propanamide A 500 mL three-neck round bottom flask equipped with a stir bar, thermocouple, and nitrogen inlet was charged with 3-chloro-N-ethyl-1-(pyridine-3-yl)-1H-pyrazol-amine (40.10 g, 91.7 wt %, 165.1 mmol) and dichloromethane (199.1 g) making brown solution that was endothermic on mixing. 3-((3,3,3-Trifluoropropyl)thio)propanoic acid (52.51 g, 70.0 wt %, 166.6 mmol) was added via syringe pump over 20 minutes keeping the temperature below 30° C. The reaction went from clear brown, to a mustard yellow slurry, to clear brown again over the addition. After 1 hour, water (123.3 g) was added followed by 20 wt % sodium hydroxide (40.3 g). The pH was tested and was ~13. After mixing for 15 minutes the layers were allowed to separate over 50 minutes. The aqueous layer (172.1 g) was treated with methanol (119.62 g) and 2 N hydrochloric acid (28.20 g) giving a clear solution with pH~1 (320.0 g, 0.1 wt % active, 0.3730 g active, 0.5% yield loss). The organic layer (278.1 g) was collected into a 500 mL flask for distillation. A distillation head was attached to the 500 mL three neck round bottomed flask containing the organic layer. Approximately ⅔ of the dichloromethane was distilled then methanol was added with continued distillation to remove residual dichloromethane and toluene. The distillation was continued until the toluene was less than 2.5 wt %. An in pot yield was determined once the dichloromethane and toluene had been exchanged with methanol (98.49 g methanol solution, 65.2 wt % by HPLC internal assay, 64.2 g active, 95.8% in process yield). Into the flask containing the solution of crude N-(3-chloro-1-(pyridin-3-yl)-1H-pyrazol-4-yl)-N-ethyl-3-((3,3,3-trifluoropropyl)thio)-propanamide was added methanol (61.82 g) to get a 40 wt % solution and the flask was equipped with a nitrogen inlet and overhead stirrer (banana blade) at 227 RPM. Water (35.23 g) was added all at once and the solution was seeded with N-(3-chloro-1-(pyridin-3-yl)-1H-pyrazol-4-yl)-N-ethyl-3-((3,3,3-trifluoropropyl)thio)propanamide (96 mg) at 26.8° C. After stirring overnight at room temperature the dark brown slurry was cooled to 1° C. with and ice bath for 5 hours. The solids were isolated by filtration through a coarse glass frit. The chocolate brown sandy solids were washed with cold 1:1 v:v methanol/water (80 mL, 74.2 g). The wet cake (70.58 g) was allowed to air dry overnight to constant mass giving the titled compound as brown solids (52.3 g, 94.1 wt % by HPLC internal standard assay, 49.23 g active, 73.5% yield).

Example 9

3-((3,3,3-Trifluoropropyl)thio)propanoic acid

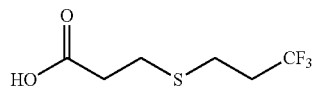

A 100 mL, 3-neck round bottom flask was charged with 3-bromopropanoic acid (500 mg, 3.27 mmol) and methanol (10 mL), potassium hydroxide (KOH, 403 mg, 7.19 mmol) was added, followed by 3,3,3-trifluoropropane-1-thiol (468 mg, 3.60 mmol). The mixture was heated at 50° C. for 4 hours, after which it was acidified with 2 N hydrochloric acid and extracted with methyl tert-butylether (MTBE, 2×10 mL). The organic layer was concentrated to dryness to afford a light yellow oil (580 mg, 88%): $^1$H NMR (400 MHz, CDCl$_3$) δ 2.83 (td, J=7.1, 0.9 Hz, 2H), 2.78-2.64 (m, 4H), 2.48-2.32 (m, 2H).

Alternate Synthetic Route to:
3-((3,3,3-Trifluoropropyl)thio)propanoic acid

A 100 mL stainless steel Parr reactor was charged with azobisisobutyronitrile (AIBN, 0.231 g, 1.41 mmol), toluene (45 mL), 3-mercaptopropionic acid (3.40 g, 32.0 mmol), and octanophenone (526.2 mg) as an internal standard and was purged and pressure checked with nitrogen. The reactor was cooled with dry ice and the 3,3,3-trifluoropropene (3.1 g, 32.3 mmol) was condensed into the reactor. The ice bath was removed and the reactor heated to 60° C. and stirred for 27 hours. The internal yield of the reaction was determined to be 80% by use of the octanophenone internal standard. The pressure was released and the crude mixture removed from the reactor. The mixture was concentrated by rotary evaporation and 50 mL of 10% sodium hydroxide was added. The solution was washed with methyl tert-butylether (50 mL) then acidified to pH~1 with 6 N hydrochloric acid. The product was extracted with 100 mL methyl tert-butylether, dried over magnesium sulfate (MgSO$_4$), filtered, and concentrated to give the crude titled compound as an oil (5.34 g, 26.4 mmol, 83%, 87.5 area % on GC): $^1$H NMR (400 MHz, CDCl$_3$) δ 2.83 (td, J=7.1, 0.9 Hz, 2H), 2.76-2.64 (m, 4H), 2.47-2.30 (m, 2H); $^{13}$C NMR (101 MHz, CDCl$_3$) δ 177.68, 125.91 (q, J=277.1 Hz), 34.58 (q, J=28.8 Hz), 34.39, 26.63, 24.09 (q, J=3.3 Hz); $^{19}$F NMR (376 MHz, CDCl$_3$) δ −66.49.

Alternate Synthetic Route to:
3-((3,3,3-Trifluoropropyl)thio)propanoic acid

A 250 mL three-neck round bottomed flask was charged with toluene (81 mL) and cooled to <−50° C. with a dry ice/acetone bath. 3,3,3-Trifluoropropene (10.28 g, 107.0 mmol) was bubbled into the solvent and the ice bath was removed. 3-Mercaptopropionic acid (9.200 g, 86.70 mmol) and 2,2-dimethoxy-2-phenylacetophenone (1.070 g, 4.170 mmol) was added and the long wave light (366 nm, 4 watt UVP lamp) was turned on (Starting temperature: −24° C.). The reaction reached a high temperature of 27.5° C. due to heat from the lamp. The reaction was stirred with the black light on for 4 hours. After 4 hours the black light was turned off and the reaction concentrated by rotary evaporation (41° C., 6 mm Hg) giving a pale yellow oil (18.09 g, 51:1 linear:branched isomer, 90 wt % linear isomer by GC internal standard assay, 16.26 g active, 93%). The crude material was dissolved in 10% sodium hydroxide w/w (37.35 g) and was washed with toluene (30 mL) to remove non-polar impurities. The aqueous layer was acidified to pH~2-3 with hydrochloric acid (2 N, 47.81 g) and was extracted with toluene (50 mL). The organic layer was washed with water (40 mL) and dried over magnesium sulfate, filtered, and concentrated by rotary evaporation giving a pale yellow oil (14.15 g, 34:1 linear:branched isomer, 94 wt % linear isomer by GC internal standard assay, 13.26 g active, 76%).

Alternative Synthesis of:
3-((3,3,3-Trifluoropropyl)thio)propanoic acid

A 100 mL stainless steel Parr reactor was charged with 3-mercaptopropionic acid (3.67 g, 34.6 mmol), toluene (30.26 g), and 2,2'-azobis(4-methoxy-2,4-dimethyl) valeronitrile (V-70, 0.543 g, 1.76 mmol) and the reactor was cooled with a dry ice/acetone bath, purged with nitrogen, and pressure checked. 3,3,3-Trifluoropropene (3.20 g, 33.3 mmol) was added via transfer cylinder and the reaction was allowed to warm to 20° C. After 24 hours, the reaction was heated to 50° C. for 1 hour to decompose any remaining V-70 initiator. The reaction was allowed to cool to room temperature. The solution was concentrated by rotary evaporation to provide the title compound (6.80 g, 77.5 wt % linear isomer by GC internal standard assay, 5.27 g active, 76%, 200:1 linear:branched by GC, 40:1 linear:branched by fluorine NMR)

Example 10

Methyl-3-((3,3,3-trifluoropropyl)thio)propionate
(Compound 10.6)

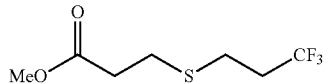 [SMILES: COC(=O)CCSCCC(F)(F)F]

A 100 mL stainless steel Parr reactor was charged with azobisisobutyronitrile (0.465 g, 2.83 mmol), toluene (60 mL) and methyl-3-mercaptopropionate (7.40 g, 61.6 mmol) and was purged and pressure checked with nitrogen. The reactor was cooled with dry ice and the 3,3,3-trifluopropopene (5.7 g, 59.3 mmol) was condensed into the reactor. The ice bath was removed and the reactor heated to 60° C. and stirred to 24 hours. The heat was turned off and the reaction left at room temperature overnight. The mixture was removed from the reactor and concentrated to a yellow liquid. The liquid was distilled by vacuum distillation (2 Torr, 85° C.) and three fractions were collected: fraction 1 (1.3 g, 6.01 mmol, 10%, 70.9 area % by GC), fraction 2 (3.7 g, 17.1 mmol, 29%, 87 area % by GC), and fraction 3 (4.9 g, 22.7 mmol, 38%, 90.6 area % by GC): $^1$H NMR (400 MHz, CDCl$_3$) δ 3.71 (s, 3H), 2.82, (td, J=7.3, 0.7 Hz, 2H), 2.75-2.68 (m, 2H), 2.63 (td, J=7.2, 0.6 Hz, 2H), 2.47-2.31 (m, 2H); $^{13}$C NMR (101 MHz, CDCl$_3$) δ 172.04, 125.93 (q, J=277.2 Hz), 51.86, 34.68 (q, J=28.6 Hz), 34.39, 27.06, 24.11 (q, J=3.3 Hz); $^{19}$F NMR (376 MHz, CDCl$_3$) δ −66.53.

Alternate Synthetic Route to: Methyl-3-((3,3,3-trifluoropropyl)thio)propionate A 500 mL three-neck round bottomed flask was charged with toluene (200 mL) and cooled to <−50° C. with a dry ice/acetone bath. 3,3,3-Trifluoropropene (21.8 g, 227 mmol) was condensed into the reaction by bubbling the gas through the cooled solvent and the ice bath was removed. Methyl 3-mercaptopropionate (26.8 g, 223 mmol) and 2,2-dimethoxy-2-phenylacetophenone (2.72 g, 10.61 mmol) were added and a UVP lamp (4 watt) that was placed within 2 centimeters of the glass wall was turned on to the long wave function (366 nanometers). The reaction reached 35° C. due to heat from the lamp. After 4 hours, all of the trifluoropropene was either consumed or boiled out of the reaction. The light was turned off and the reaction stirred at room temperature overnight. After 22 hours, more trifluoropropene (3.1 g) was bubbled through the mixture at room temperature and the light was turned on for an additional 2 hours. The reaction had converted 93% so no more trifluoropropene was added. The light was turned off and the mixture concentrated on the rotovap (40° C., 20 torr) giving a yellow liquid (45.7 g, 21.3:1 linear:branched isomer, 75 wt % pure linear isomer determined by a GC internal standard assay, 34.3 g active, 71% in pot yield).

Alternate Synthetic Route to: Methyl-3-((3,3,3-trifluoropropyl)thio)propionate A 100 mL stainless steel Parr reactor was charged with methyl 3-mercaptopropionate (4.15 g, 34.5 mmol), toluene (30.3 g), and 2,2'-azobis(4-methoxy-2,4-dimethyl) valeronitrile (V-70, 0.531 g, 1.72 mmol) and the reactor was cooled with a dry ice/acetone bath, purged with nitrogen, and pressure checked. 3,3,3-Trifluoropropene (3.40 g, 35.4 mmol) was added via transfer cylinder and the reaction was allowed to warm to 20° C. After 23 hours the reaction was heated to 50° C. for 1 hour to decompose any remaining V-70 initiator. The reaction was allowed to cool to room temperature. The solution was concentrated to provide the title compound (7.01 g, 66%, 70.3 wt % linear isomer by GC internal standard assay, 4.93 g active, 66%, 24:1 linear:branched by GC, 18:1 linear:branched by fluorine NMR)

Example 11

N-(3-Chloro-1-(pyridin-3-yl)-1H-pyrazol-4-yl)-N-ethyl-3-((3,3,3-trifluoropropyl)sulfoxo)propanamide (Compound 11.6)

N-(3-Chloro-1-(pyridin-3-yl)-1H-pyrazol-4-yl)-N-ethyl-3-((3,3,3-trifluoropropyl)thio) propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate ($Na_2CO_3$). The organic layer was dried over sodium sulfate and concentrated under reduced pressure to provide a thick yellow oil. The crude product was purified by flash column chromatography using 0-10% methanol/ethyl acetate as eluent. The pure fractions were combined and concentrated to afford the desired product as an oil (42.6 g, 68%): $^1$H NMR (400 MHz, DMSO-$d_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); ESIMS m/z 423 ([M+H]$^+$).

Example 12

Methyl 3-chloro-1-(pyridin-3-yl)-4,5-dihydro-1H-pyrazole-5-carboxylate (6c)

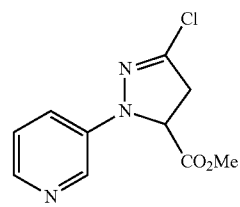 [SMILES: COC(=O)C1CC(Cl)=NN1c1cccnc1]

(E)-2-(2-(Pyridin-3-yl)hydrazono)acetic acid hydrochloride (13.6 g, 64.1 mmol) was stirred in ethyl acetate (250 mL). N-chlorosuccinimide (17.9 g, 131 mmol) was added and the reaction stirred for 10 minutes. Methyl acrylate (35.2 mL, 385 mmol) was added followed by addition of potassium bicarbonate (19.4 g, 192 mmol). Water (0.05 mL) was added and the mixture stirred at 18° C. The reaction temperature rose from 18 to 21° C. over 1 hour and the reaction was stirred for 20 hours. Water (300 mL) and saturated aqueous sodium carbonate (~100 mL) were added. The mixture was filtered through Celite® and the filtrate was extracted with ethyl acetate (2×500 mL). The organic layers were dried and concentrated. The residue was purified by flash column chromatography using 50-100% ethyl acetate/hexanes as eluent to afford the desired product as an orange oil (10.1 g, 62.5%): $^1$H NMR (400 MHz, CDCl$_3$) δ 8.30 (dd, J=2.9, 0.7 Hz, 1H), 8.18 (dd, J=4.7, 1.4 Hz, 1H), 7.38 (ddd, J=8.4, 2.9, 1.4 Hz, 1H), 7.19 (ddd, J=8.5, 4.7, 0.7 Hz, 1H), 4.81 (dd, J=12.4, 6.9 Hz, 1H), 3.79 (s, 3H), 3.56 (dd, J=17.8, 12.4 Hz, 1H), 3.34 (dd, J=17.8, 6.9 Hz, 1H); ESIMS m/z 240 ([M+H]$^+$).

Example 13

Methyl 3-chloro-1-(pyridin-3-yl)-1H-pyrazole-5-carboxylate (6d)

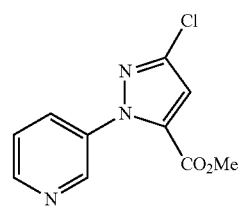 [SMILES: COC(=O)c1cc(Cl)nn1-c1cccnc1]

Methyl 3-chloro-1-(pyridine-3-yl)-4,5-dihydro-1H-pyrazole-5-carboxylate (2.63 g, 11.0 mmol) was stirred in tetrahydrofuran (50 mL) and water (50 mL) at 0° C. diammonium cerium (IV) nitrate (15.0 g, 27.4 mmol) was added in portions and the reaction was stirred at room temperature for 18 hours. thin layer chromatography analysis indicated that the starting material was consumed. The mixture was extracted with ethyl acetate (2×300 mL) and the organic layers were dried and concentrated. The residue was purified by flash column chromatography using 50-100% ethyl acetate/hexanes as eluent. The pure fractions were concentrated to provide the desired product as a yellow solid (1.50 g, 52%): mp 99-102° C.; $^1$H NMR (400 MHz, DMSO-$d_6$) δ 9.00 (dd, J=2.5, 0.7 Hz, 1H), 8.83 (dd, J=5.2, 1.5 Hz, 1H), 8.35 (ddd, J=8.3, 2.5, 1.4 Hz, 1H), 7.83 (ddd, J=8.3, 5.2, 0.7 Hz, 1H), 7.35 (s, 1H), 3.78 (s, 3H); $^{13}$C NMR (101 MHz, CDCl$_3$) δ 158.34, 149.90, 146.89, 141.39, 136.09, 134.77, 133.30, 123.14, 112.01, 52.53; ESIMS m/z 238 ([M+H]$^+$).

Alternate Synthetic Route to: Methyl 3-chloro-1-(pyridin-3-yl)-1H-pyrazole-5-carboxylate Methyl 3-chloro-1-(pyridine-3-yl)-4,5-dihydro-1H-pyrazole-5-carboxylate (0.500 g, 2.09 mmol) was stirred in acetone (10 mL). potassium permanganate (0.330 g, 2.09 mmol) was added in one portion and the reaction was stirred at room temperature overnight, at which point thin layer chromatography analysis (70% ethyl acetate/hexanes) indicated that the reaction was <50% complete. Additional potassium permanganate (520 mg, 3.29 mmol) was added and the reaction was stirred for an additional 4 hours. The mixture was filtered and concentrated and the residue was partitioned between ethyl acetate and water. The organic portion was dried over sodium sulfate, filtered, and concentrated. The residue was purified flash column chromatography using 80-100% ethyl acetate/hexanes as eluent to provide the desired product as a white solid (180 mg 36%).

Example 14

3-Chloro-1-(pyridine-3-yl)-1H-pyrazole-5-carboxylic acid hydrochloride (6e)

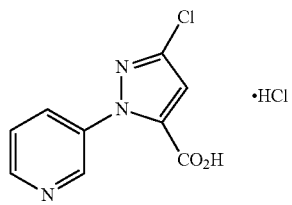 [SMILES: O=C(O)c1cc(Cl)nn1-c1cccnc1 ; Cl]

Methyl 3-chloro-1-(pyridin-3-yl)-1H-pyrazole-5-carboxylate (3.83 g, 16.1 mmol) was stirred in dioxane (53.7 mL). The orange suspension was heated until a solution was achieved. Lithium hydroxide hydrate (1.01 g, 24.2 mmol) in water (26.9 mL) was added to afford a darker red solution. The reaction was stirred at room temperature for 1 hours, at which point LCMS showed the corresponding acid to be the major product. The orange mixture was concentrated to dryness and the residue was mixed with 4 N hydrochloric acid in dioxane (100 mL). The suspension was heated to reflux for 1 hour and allowed to cool to room temperature. The resulting suspension was filtered and the filter cake was rinsed with dioxane. The solid was vacuum dried at 50° C. to afford the desire product as a white solid (4.00 g, 91%): mp 244-246° C.; $^1$H NMR (400 MHz, DMSO-$d_6$) δ 9.00 (dd, J=2.5, 0.7 Hz, 1H), 8.82 (dd, J=5.2, 1.4 Hz, 1H), 8.35 (ddd, J=8.3, 2.4, 1.4 Hz, 1H), 7.85 (ddd, J=8.3, 5.2, 0.7 Hz, 1H), 7.25 (s, 1H); $^{13}$C NMR (101 MHz, DMSO-$d_6$) δ 158.71, 146.00, 143.44, 140.36, 137.00, 136.83, 125.19, 111.71; ESIMS m/z 224 ([M+H]$^+$).

Alternate Synthetic Route to: 3-Chloro-1-(pyridine-3-yl)-1H-pyrazole-5-carboxylic acid hydrochloride Methyl 3-chloro-1-(pyridin-3-yl)-1H-pyrazole-5-carboxylate (1.5 g, 6.0 mmol) was stirred in concentrated hydrochloric acid (25 mL). The reaction mixture was heated at reflux to afford a yellow solution. After heating overnight a solid had precipitated, and LCMS analysis of the mixture indicated that the reaction was complete. The mixture was allowed to cool to room temperature and dioxane (50 mL) was added. The mixture was concentrated to dryness. acetonitrile (50 mL) was added and the resulting mixture was concentrated. The residue was vacuum dried at 40° C. to afford the desired product as a yellow solid (1.6 g, 97%).

Alternate Synthetic Route to: 3-Chloro-1-(pyridine-3-yl)-1H-pyrazole-5-carboxylic acid hydrochloride A 3-neck round bottomed flask (100 mL) was charged with ethyl 3-chloro-1-(pyridin-3-yl)-1H-pyrazole-5-carboxylate (0.200 g, 0.795 mmol) and hydrochloric acid (37%, 4 mL). The reaction was heated at 90° C. for 18 hours and allowed to cool to 20° C. Dioxane (5 mL) was added to the resulting suspension and was concentrated to dryness. Dioxane (5 mL) was added and the suspension was concentrated again to afford a white solid. Dioxane (5 mL) was added and the resulting suspension was stirred for 1 hour at 20° C. The solid was filtered and the solid was rinsed with dioxane (2 mL). The filter cake was dried under vacuum at 20° C. to afford the title compound as a white solid (0.218 g, 100%): $^1$H NMR (400 MHz, DMSO-$d_6$) δ 9.05 (dd, J=2.5, 0.7 Hz, 1H), 8.84 (dd, J=5.3, 1.4 Hz, 1H), 8.41 (ddd, J=8.3, 2.5, 1.4 Hz, 1H), 7.88 (ddd, J=8.3, 5.2, 0.7 Hz, 1H), 7.26 (s, 1H); $^{13}$C NMR (101 MHz, DMSO-$d_6$) δ 158.71, 146.00, 143.44, 140.36, 137.76, 137.00, 136.83, 125.19, 111.71.

Example 15

3-((3,3,3-Trifluoropropyl)thio)propanoyl chloride

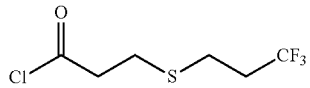 [SMILES: O=C(Cl)CCSCCC(F)(F)F]

A dry 5 L round bottom flask equipped with magnetic stirrer, nitrogen inlet, reflux condenser, and thermometer, was charged with 3-((3,3,3-trifluoropropyl)thio)propanoic acid (188 g, 883 mmol) in dichloromethane (3 L). Thionyl chloride (525 g, 321 mL, 4.42 mol) was then added dropwise over 50 minutes. The reaction mixture was heated to reflux (about 36° C.) for 2 hours, then cooled to room temperature. Concentration under vacuum on a rotary evaporator, followed by distillation (40 Torr, product collected from 123-127° C.) gave the title compound as a clear colorless liquid (177.3 g, 86%): $^1$H NMR (400 MHz, CDCl$_3$) δ 3.20 (t, J=7.1 Hz, 2H), 2.86 (t, J=7.1 Hz, 2H), 2.78-2.67 (m, 2H), 2.48-2.31 (m, 2H); $^{19}$F NMR (376 MHz, CDCl$_3$) δ −66.42, −66.43, −66.44, −66.44.

Example 16

3-(((2,2-Difluorocyclopropyl)methyl)thio)propanoic acid

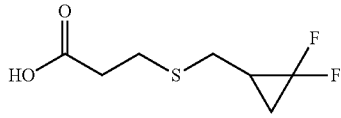 [SMILES: O=C(O)CCSCC1CC1(F)F]

Powdered potassium hydroxide (423 mg, 7.54 mmol) and 2-(bromomethyl)-1,1-difluorocyclopropane (657 mg, 3.84 mmol) were sequentially added to a stirred solution of 3-mercaptopropanoic acid (400 mg, 3.77 mmol) in methanol (2 mL) at room temperature. The resulting white suspension was stirred at 65° C. for 3 hours and quenched with 1N aqueous hydrochloric acid and diluted with ethyl acetate. The organic phase was separated and the aqueous phase extracted with ethyl acetate (2×50 mL). The combined organic extracts were dried over magnesium sulfate, filtered and concentrated in vacuo to give the title molecule as a colorless oil (652 mg, 84%): IR (KBr thin film) 3025, 2927, 2665, 2569, 1696 cm$^{-1}$; $^1$H NMR (400 MHz, CDCl$_3$) δ 2.85 (t, J=7.0 Hz, 2H), 2.82-2.56 (m, 4H), 1.88-1.72 (m, 1H), 1.53 (dddd, J=12.3, 11.2, 7.8, 4.5 Hz, 1H), 1.09 (dtd, J=13.1, 7.6, 3.7 Hz, 1H); ESIMS m/z 195.1 ([M−H]$^-$).

Example 17

3-(((2,2-Difluorocyclopropyl)methyl)thio)propanoyl chloride

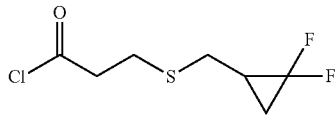 [SMILES: O=C(Cl)CCSCC1CC1(F)F]

In a 3 L 3-neck round bottomed-flask equipped with an overhead stirrer, a temperature probe, and addition funnel and an nitrogen inlet was charged with 3-(((2,2-difluorocyclopropyl)methyl)thio)propanoic acid (90.0 g, 459 mmol) that was immediately taken up in dichloromethane (140 mL) with stirring. At room temperature, thionyl chloride (170 mL, 2293 mmol) in dichloromethane (100 mL) was added drop-wise with stirring. The reaction mixture was heated to 40° C. and heated for 2 hours. The reaction was determined to be complete by $^1$H NMR (An aliquot of the reaction mixture was taken, and concentrated down via rotary evaporator). The reaction was allowed to cool to room temperature and the mixture was transferred to a dry 3 L round-bottom and concentrated via the rotary evaporator. This resulted in 95 g of a honey-colored oil. The contents were gravity filtered through paper and the paper rinsed with diethyl ether (10 mL). The rinse was added to the flask. This gave a clear yellow liquid. The liquid was placed on a rotary evaporator to remove the ether. This gave 92.4 g of a yellow oil. The oil was Kugelrohr distilled (bp 100-110° C./0.8-0.9 mm Hg) to provide the title compound as a colorless oil (81.4 g, 81%): $^1$H NMR (400 MHz, CDCl$_3$) δ 3.27-3.12 (m, 2H), 2.89 (t, J=7.1 Hz, 2H), 2.67 (ddd, J=6.8, 2.6, 1.0 Hz, 2H), 1.78 (ddq, J=13.0, 11.3, 7.4 Hz, 1H), 1.64-1.46 (m, 1H), 1.09 (dtd, J=13.2, 7.7, 3.7 Hz, 1H).

Example 18

Ethyl 5-oxo-2-(pyridin-3-yl)pyrazolidine-3-carboxylate (Compound 18.6)

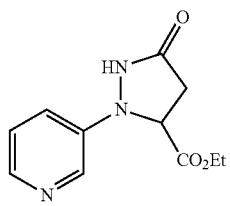 [SMILES: CCOC(=O)C1CC(=O)NN1c1cccnc1]

A 4-neck round bottomed flask (250 mL) was charged with sodium ethoxide (21 wt % in ethanol, 56 mL, 192 mmol). 3-Hydrazinopyridine.dihydrochloride (10.0 g, 55.0 mmol) was added, causing an exotherm from 20° C. to 32° C. The reaction was allowed to cool to 20° C. and diethyl maleate (13.4 mL, 82.0 mmol) was added, and the reaction was heated at 60° C. for 3 hours. The reaction was cooled to 20° C. and quenched with acetic acid. The reaction mixture was diluted with water (100 mL) and extracted with ethyl acetate (3×100 mL). The combined organics were concentrated to dryness and the residue was purified by flash column chromatography using ethyl acetate as eluent to the title compound as a blue oil (6.60 g, 51%): $^1$H NMR (400 MHz, DMSO-d$_6$) δ 10.40 (s, 1H), 8.40-8.26 (m, 1H), 8.19 (dd, J=4.4, 1.6 Hz, 1H), 7.47-7.21 (m, 2H), 4.77 (dd, J=9.8, 2.1 Hz, 1H), 4.22 (qd, J=7.1, 1.7 Hz, 2H), 3.05 (dd, J=17.0, 9.8 Hz, 1H), 1.99 (s, 1H), 1.25 (t, J=7.1 Hz, 3H); $^{13}$C NMR (101 MHz, DMSO-d$_6$) δ 170.37, 146.60, 142.60, 137.28, 123.54, 121.94, 65.49, 61.32, 32.15, 20.72, 13.94; ESIMS m/z 236 ([M+H]$^+$).

Example 19

Ethyl 3-chloro-1-(pyridin-3-yl)-4,5-dihydro-1H-pyrazole-5-carboxylate (Compound 19.6)

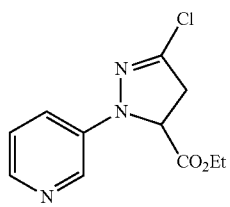 [SMILES: CCOC(=O)C1CC(Cl)=NN1c1cccnc1]

A 3-neck round bottomed flask (100 mL) was charged with ethyl 5-oxo-2-(pyridin-3-yl)pyrazolidine-3-carboxylate (8.50 g, 36.1 mmol) and acetonitrile (40 mL). Phosphoryl trichloride (4.05 mL, 43.4 mmol) was charged and the reaction was heated at 60° C. for 2 hours. The reaction was cooled to 20° C. and water (100 mL) was added. Sodium carbonate was added to adjust pH to 8 and the mixture was extracted with ethyl acetate (3×100 mL). The organic layers were concentrated to dryness and the residue was purified by flash column chromatography using 30-80% ethyl acetate/hexanes as eluent to provide the title compound as a yellow oil (7.30 g, 79%): $^1$H NMR (400 MHz, CDCl$_3$) δ 8.30 (dd, J=2.9, 0.8 Hz, 1H), 8.17 (dd, J=4.7, 1.4 Hz, 1H), 7.38 (ddd, J=8.4, 2.8, 1.4 Hz, 1H), 7.18 (ddd, J=8.4, 4.7, 0.7 Hz, 1H), 4.79 (dd, J=12.4, 6.9 Hz, 1H), 4.24 (qd, J=7.1, 1.1 Hz, 2H), 3.55 (dd, J=17.7, 12.4 Hz, 1H), 3.33 (dd, J=17.8, 6.9 Hz, 1H), 1.25 (t, J=7.1 Hz, 3H); $^{13}$C NMR (101 MHz, CDCl$_3$) δ 169.65, 141.90, 141.33, 141.09, 135.13, 123.53, 120.37, 62.89, 62.35, 42.45, 14.03; ESIMS m/z 254 ([M+H]$^+$).

Example 20

Ethyl 3-chloro-1-(pyridin-3-yl)-1H-pyrazole-5-carboxylate

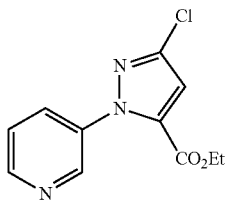 [SMILES: CCOC(=O)c1cc(Cl)nn1-c1cccnc1]

A 3-neck round bottomed flask (100 mL) was charged with ethyl 3-chloro-1-(pyridin-3-yl)-1H-dihydropyrazole-5-carboxylate (2.00 g, 7.88 mmol) and acetonitrile (20 mL). Manganese (IV) oxide (3.43 g, 39.4 mmol) was added, causing an exotherm from 20° C. to 21° C. The reaction was stirred at 60° C. for 18 hours. Additional manganese (IV) oxide (3.43 g, 39.4 mmol) was added and the reaction was stirred at 80° C. for 6 hours. The mixture was filtered through a Celite® pad and the pad was rinsed with ethyl acetate (20 mL). The combined filtrates were concentrated to dryness and the residue was purified by flash column chromatography using 10-60% ethyl acetate/hexanes. The pure fractions were concentrated to dryness to afford a white solid after drying (1.84 g, 93%): $^1$H NMR (400 MHz, CDCl$_3$) δ 8.75-8.64 (m, 2H), 7.79 (ddd, J=8.2, 2.6, 1.5 Hz, 1H), 7.42 (ddd, J=8.2, 4.8, 0.8 Hz, 1H), 6.98 (s, 1H), 4.27 (q, J=7.1 Hz, 2H), 1.27 (t, J=7.1 Hz, 3H); $^{13}$C NMR (101 MHz, CDCl$_3$) δ 157.90, 149.88, 147.01, 141.41, 136.24, 135.27, 133.34, 123.11, 111.97, 61.87, 13.98; ESIMS m/z 252 ([M+H]$^+$).

Alternate Synthetic Route to: Ethyl 3-chloro-1-(pyridin-3-yl)-1H-pyrazole-5-carboxylate A vial (20 mL) was charged with ethyl 3-chloro-1-(pyridin-3-yl)-1H-dihydropyrazole-5-carboxylate (0.500 g, 1.97 mmol) and acetonitrile (5 mL). Sodium persulfate (0.799 g, 2.96 mmol) was added, followed by sulfuric acid (0.733 g, 7.88 mmol) (Exotherm!). The reaction was heated at 60° C. for 18 hours. The reaction was cooled to 20° C. and poured into water (20 mL). The mixture was basified with sodium carbonate to pH 9 and extracted with ethyl acetate (2×20 mL). The organic layers were concentrated to a residue, which was purified by flash column chromatography using 50% ethyl acetate/hexanes as eluent to provide the title compound as a white solid (0.280 g, 56%).

Method Examples

Example A

Bioassays on Green Peach Aphid ("GPA") (*Myzus persicae*) (MYZUPE.)

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four posts with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

Corrected % Control=100*(X−Y)/X where
X=No. of live aphids on solvent check plants and
Y=No. of live aphids on treated plants
The results are indicated in the table entitled "Table 1: GPA (MYZUPE) and sweetpotato whitefly-crawler (BEMITA) Rating Table".

Example B

Bioassays on Sweetpotato Whitefly Crawler (*Bemisia tabaci*) (BEMITA.)

The sweetpotato whitefly, *Bemisia tabaci* (Gennadius), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective pesticides.

Cotton plants grown in 3-inch pots, with 1 small (3-5 cm) true leaf, were used at test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Pesticidal activity was measured by using Abbott's correction formula (see above) and presented in Table 1.

TABLE 1

GPA (MYZUPE) and sweetpotato whitefly-crawler (BEMITA) Rating Table

| Example Compound | BEMITA | MYZUPE |
| --- | --- | --- |
| 6a | B | B |
| 6b | D | B |
| 6c | A | B |
| 6d | D | B |
| 6e | D | B |
| Compound 8.6 | A | A |
| Compound 11.6 | A | A |
| Compound 18.6 | B | B |
| Compound 19.6 | B | B |

| % Control of Mortality | Rating |
| --- | --- |
| 80-100 | A |
| More than 0-Less than 80 | B |
| Not Tested | C |
| No activity noticed in this bioassay | D |

Comparative Examples

Example CE-5

3-Chloro-N-ethyl-1-(pyridin-3-yl)-1H-pyrazol-amine

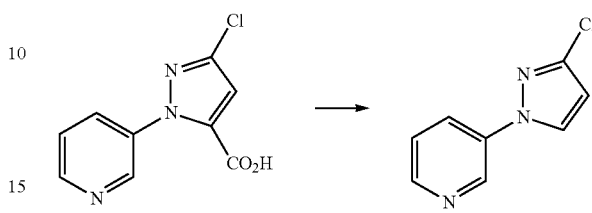

Attempted Decarboxylation with Sulfuric Acid:
3-Chloro-1-(pyridin-3-yl)-1H-pyrazole-5-carboxylic acid hydrochloride (1.00 g, 2.50 mmol) was dissolved in warm sulfolane (12.5 mL). sulfuric acid (1.35 mL, 25.0 mmol) was added and the reaction mixture was heated to 100° C. After stifling for 1 hour, LCMS indicated that the reaction did not occur. The reaction was further heated at 130° C. for 2 hour, at which point LCMS indicated no change. Additional sulfuric acid (4 mL) was added and the reaction was heated at 150° C. for 2 hour, at which point LCMS showed a new major peak that did not correspond to desired product.

Attempted Decarboxylation with Palladium (II) Trifluoroacetate/Trifluoroacetic Acid:
3-Chloro-1-(pyridin-3-yl)-1H-pyrazole-5-carboxylic acid hydrochloride (1.00 g, 2.50 mmol) was dissolved in a mixture of dimethylsulfoxide (0.625 mL) and N,N-dimethylformamide (11.9 ml). Trifluoroacetic acid (1.93 ml, 25.0 mmol) was added followed by the addition of palladium(II) trifluoroacetate (0.332 g, 1.00 mmol). The reaction was heated at 100° C. overnight, at which time LCMS indicated that a reaction had occurred but no desired product had been formed.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A process comprising:
(a) reacting 3-hydrazinopyridine dihydrochloride with glyoxylic acid to yield (E)-2-(2-(pyridin-3-yl)hydrazono) acetic acid (6a)

(6a)

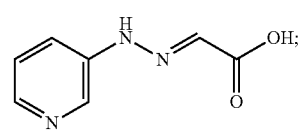

(b) reacting (E)-2-(2-(pyridin-3-yl)hydrazono)acetic acid (6a) with acrylonitrile and a source of chlorine, in the presence of a base, to yield 3-chloro-1-(pyridin-3-yl)-4, 5-dihydro-1H-pyrazole-5-carbonitrile (6b)

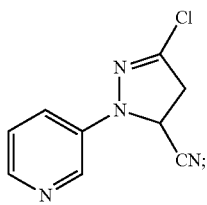
(6b)

(c) dehydrocyanating 3-chloro-1-(pyridin-3-yl)-4,5-dihydro-1H-pyrazole-5-carbonitrile (6b), in the presence of a base, to yield 3-(3-chloro-1H-pyrazol-1-yl)pyridine (5b)

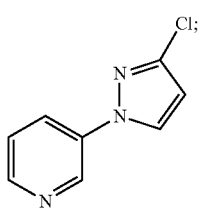
(5b)

(d) nitrating 3-(3-chloro-1H-pyrazol-1-yl)pyridine (5b) with nitric acid ($HNO_3$) to yield 3-(3-chloro-4-nitro-1H-pyrazol-1-yl)pyridine (5c)

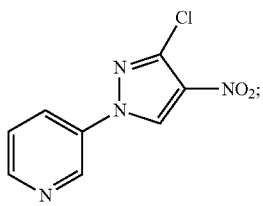
(5c)

(e) reducing 3-(3-chloro-4-nitro-1H-pyrazol-1-yl)pyridine (5c) to yield 3-chloro-1-(pyridin-3-yl)-1H-pyrazol-4-amine (5d)

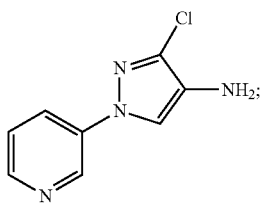
(5d)

(f) acylating 3-chloro-1-(pyridin-3-yl)-1H-pyrazol-4-amine (5d) with acetic anhydride, in the presence of an inorganic base, to yield N-(3-chloro-1-(pyridin-3-yl)-1H-pyrazol-4-yl)acetamide (1c)

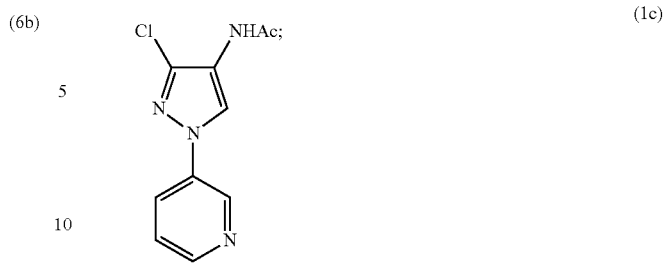
(1c)

(g) reducing N-(3-chloro-1-(pyridin-3-yl)-1H-pyrazol-4-yl)acetamide (1c) to yield 3-chloro-N-ethyl-1-(pyridin-3-yl)-1H-pyrazol-amine (1d)

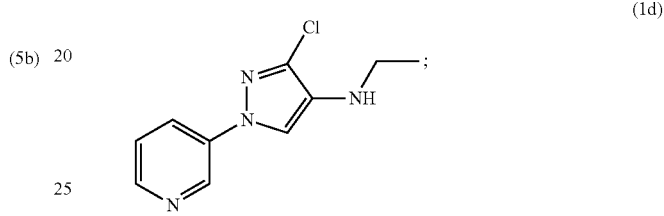
(1d)

and (h) reacting 3-chloro-N-ethyl-1-(pyridin-3-yl)-1H-pyrazol-amine (1d) with an activated carbonyl thioether of formula $X^1C(=O)C_1$-$C_4$-alkyl-S—$R^1$ wherein $R^1$ is selected from the group consisting of $C_1$-$C_4$-haloalkyl and $C_1$-$C_4$-alkyl-$C_3$-$C_6$-halocycloalkyl, and $X^1$ is selected from Cl, $OC(=O)C_1$-$C_4$ alkyl, or an activated carboxylic acid to yield pesticidal thioether (1e),

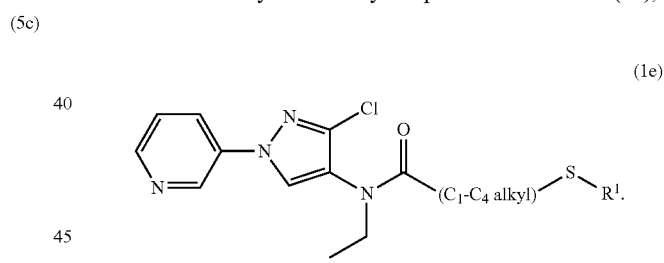
(1e)

2. A process according to claim 1 wherein 3-(3-chloro-1H-pyrazol-1-yl)pyridine (5b) is produced by the process comprising (a) reacting (E)-2-(2-(pyridin-3-yl)hydrazono)acetic acid (6a) with methyl acrylate, in the presence of a chlorine source, a base, and a sub-stoichiometric amount of water, to yield methyl 3-chloro-1-(pyridin-3-yl)-4,5-dihydro-1H-pyrazole-5-carboxylate (6c)

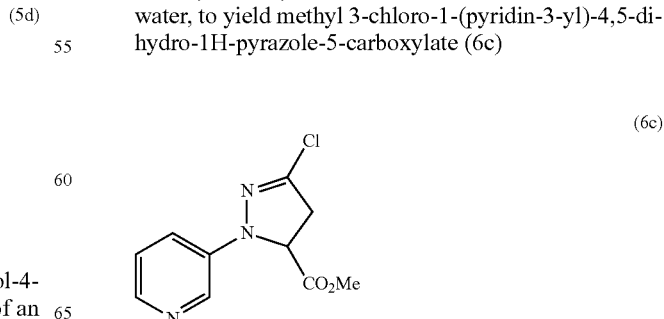
(6c)

(b) oxidizing methyl 3-chloro-1-(pyridin-3-yl)-4,5-dihydro-1H-pyrazole-5-carboxylate (6c) with diammonium cerium (IV) nitrate (CAN) to yield methyl 3-chloro-1-(pyridin-3-yl)-1H-pyrazole-5-carboxylate (6d)

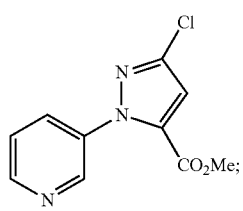

(6d)

(c) hydrolyzing methyl 3-chloro-1-(pyridin-3-yl)-1H-pyrazole-5-carboxylate (6d) to yield 3-chloro-1-(pyridin-3-yl)-1H-pyrazole-5-carboxylic acid (6e)

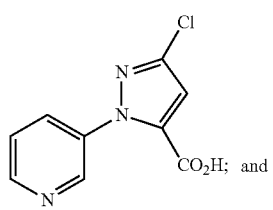

(6e)

(d) decarboxylating 3-chloro-1-(pyridin-3-yl)-1H-pyrazole-5-carboxylic acid (6e), in the presence of copper (II) oxide, to yield 3-(3-chloro-1H-pyrazol-1-yl)pyridine (5b)

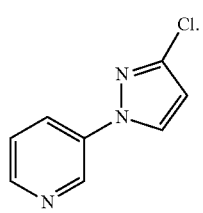

(5b)

3. A The process according to claim 1 wherein 3-(3-chloro-1H-pyrazol-1-yl)pyridine (5b) is produced by the process comprising
(a) reacting (E)-2-(2-(pyridin-3-yl)hydrazono)acetic acid (6a) with methyl acrylate, in the presence of a chlorine source, an inorganic base, and a sub-stoichiometric amount of water, to yield methyl 3-chloro-1-(pyridin-3-yl)-4,5-dihydro-1H-pyrazole-5-carboxylate (6c)

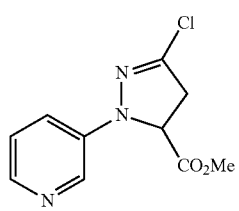

(6c)

(b) oxidizing methyl 3-chloro-1-(pyridin-3-yl)-4,5-dihydro-1H-pyrazole-5-carboxylate (6c) with diammonium cerium (IV) nitrate (CAN) to yield methyl 3-chloro-1-(pyridin-3-yl)-1H-pyrazole-5-carboxylate (6d)

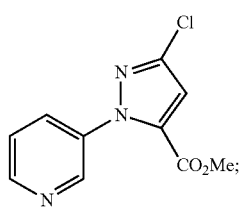

(6d)

(c) saponifying methyl 3-chloro-1-(pyridin-3-yl)-1H-pyrazole-5-carboxylate (6d) to yield 3-chloro-1-(pyridin-3-yl)-1H-pyrazole-5-carboxylic acid (6e)

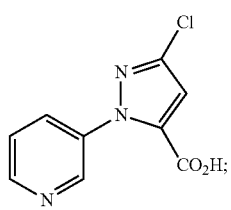

(6e)

and
(d) decarboxylating 3-chloro-1-(pyridin-3-yl)-1H-pyrazole-5-carboxylic acid (6e), in the presence of copper (II) oxide, to yield 3-(3-chloro-1H-pyrazol-1-yl)pyridine (5b)

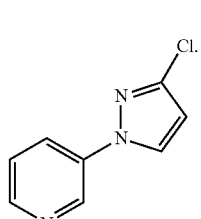

(5b)

4. The process according to claim 1, wherein $R^1$ is $CH_2CH_2CF_3$ and the suitable activated carboxylic acid, carboxylic acid anhydride, or acid chloride of a carboxylic acid is prepared from

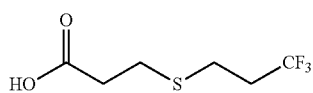

which is prepared by the photochemical free-radical coupling of 3-mercaptopropionic acid and esters thereof with 3,3,3-trifluoropropene in the presence of 2,2-dimethoxy-2-phenylacetophenone initiator and long wavelength UV light in an inert organic solvent.

5. The process according to claim 1, wherein $R^1$ is $CH_2CH_2CF_3$ and the suitable activated carboxylic acid, carboxylic acid anhydride, or acid chloride of a carboxylic acid is prepared from

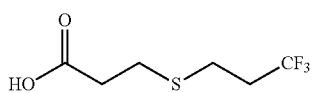

which is prepared by the low temperature free-radical initiated coupling of 3-mercapto-propionic acid with 3,3,3-trifluoropropene in the presence of 2,2'-azobis(4-methoxy-2,4-dimethyl) valeronitrile (V-70) initiator at temperatures of about −50° C. to about 40° C. in an inert organic solvent.

6. The process according to claim 1 wherein 3-chloro-N-ethyl-1-(pyridin-3-yl)-1H-pyrazol-amine (1d)

(1d)

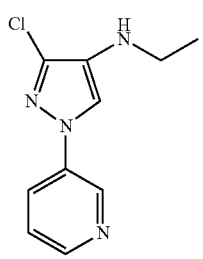

is produced by the process comprising
 (a) reacting 3-hydrazinopyridine dihydrochloride with glyoxylic acid to yield (E)-2-(2-(pyridin-3-yl)hydrazono)acetic acid (6a)

(6a)

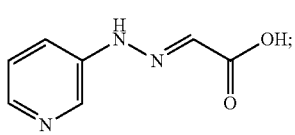

(b) reacting (E)-2-(2-(pyridin-3-yl)hydrazono)acetic acid (6a) with acrylonitrile and a source of chlorine, in the presence of a base, to yield 3-chloro-1-(pyridin-3-yl)-4,5-dihydro-1H-pyrazole-5-carbonitrile (6b)

(6b)

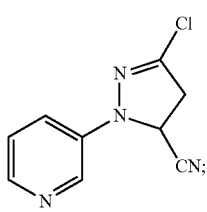

(c) dehydrocyanating of 3-chloro-1-(pyridin-3-yl)-4,5-dihydro-1H-pyrazole-5-carbonitrile (6b), in the presence of a base, to yield 3-(3-chloro-1H-pyrazol-1-yl)pyridine (5b)

(5b)

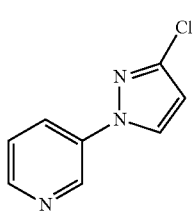

(d) nitrating 3-(3-chloro-1H-pyrazol-1-yl)pyridine (5b) with nitric acid ($HNO_3$) to yield 3-(3-chloro-4-nitro-1H-pyrazol-1-yl)pyridine (5c)

(5c)

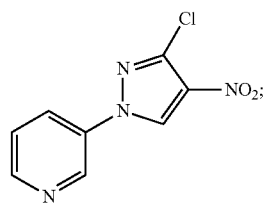

(e) reducing 3-(3-chloro-4-nitro-1H-pyrazol-1-yl)pyridine (5c) to yield 3-chloro-1-(pyridin-3-yl)-1H-pyrazol-4-amine (5d)

(5d)

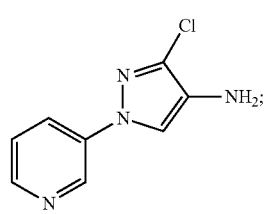

(f) acylating 3-chloro-1-(pyridin-3-yl)-1H-pyrazol-4-amine (5d) with acetic anhydride, in the presence of an inorganic base, to yield N-(3-chloro-1-(pyridin-3-yl)-1H-pyrazol-4-yl)acetamide (1c)

(1c)

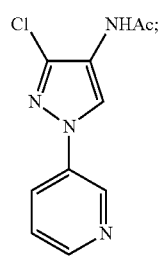

(g) alkylating N-(3-chloro-1-(pyridin-3-yl)-1H-pyrazol-4-yl)acetamide (1c) with ethyl bromide in the presence of a base to yield N-(3-chloro-1-(pyridin-3-yl)-1H-pyrazol-4-yl)-N-ethylacetamide (1c')

(1c')

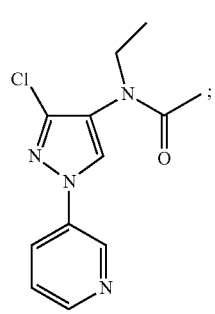

and
 (h) reacting (1c') with hydrochloric acid in water at temperatures between about 70° C. and about 90° C.

7. A The process according to claim 1 wherein 3-(3-chloro-1H-pyrazol-1-yl)pyridine (5b),

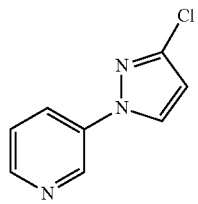
(5b)

is produced by the process comprising
a) treating 3-hydrazinopyridine.dihydrochloride with a di-$C_1$-$C_4$ alkyl maleate in a $C_1$-$C_4$ aliphatic alcohol at a temperature of about 25° C. to about 100° C. in the presence of an alkali metal $C_1$-$C_4$ alkoxide to provide pyrazolidine carboxylate

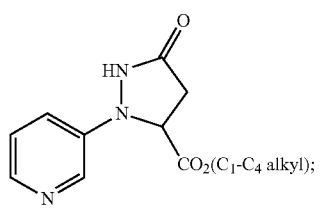
(10a)

b) treating pyrazolidine carboxylate with a chlorinating reagent in an inert organic solvent at a temperature of about 25° C. to about 100° C. to provide chlorinated dihydropyrazole carboxylate

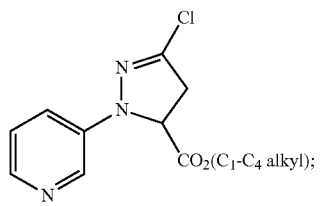
(10b)

c) treating the chlorinated dihydropyrazole carboxylate with an oxidant in an inert organic solvent at a temperature of about 25° C. to about 100° C. to provide chlorinated pyrazole carboxylate

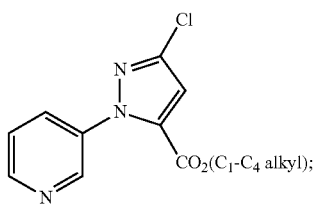
(10c)

d) treating the chlorinated pyrazole carboxylate with aqueous hydrochloric acid at a temperature of about 25° C. to about 100° C. to provide 3-chloro-1-(pyridin-3-yl)-1H-pyrazole-5-carboxylic acid hydrochloride (6e)

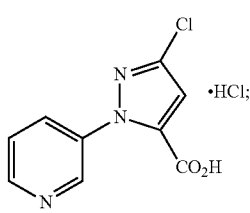
(6e)

and
e) treating 3-chloro-1-(pyridin-3-yl)-1H-pyrazole-5-carboxylic acid hydrochloride (6e) with copper(II) oxide in a polar aprotic solvent at a temperature of about 80° C. to about 140° C.

\* \* \* \* \*